US007908129B2

(12) United States Patent
Akhmatskaya et al.

(10) Patent No.: US 7,908,129 B2
(45) Date of Patent: Mar. 15, 2011

(54) METHOD, APPARATUS AND COMPUTER PROGRAM FOR MOLECULAR SIMULATION

(75) Inventors: Elena Vitalievna Akhmatskaya, Buckinghamshire (GB); Ross Howard Nobes, Cambridge (GB); Sebastian Reich, Schwielowsee (DE)

(73) Assignee: Fujitsu Limited, Kawasaki (JP)

( * ) Notice: Subject to any disclaimer, the term of this patent is extended or adjusted under 35 U.S.C. 154(b) by 63 days.

(21) Appl. No.: 12/222,382

(22) Filed: Aug. 7, 2008

(65) Prior Publication Data

US 2009/0076780 A1 Mar. 19, 2009

(30) Foreign Application Priority Data

Aug. 10, 2007 (GB) .................................. 0715659.9

(51) Int. Cl.
*G06F 17/11* (2006.01)
*G06F 17/10* (2006.01)
(52) U.S. Cl. .......................................................... 703/11
(58) Field of Classification Search .................... None
See application file for complete search history.

(56) References Cited

U.S. PATENT DOCUMENTS

| 6,021,383 A | 2/2000 | Domany et al. |
| 2003/0046050 A1 | 3/2003 | Padilla et al. |

FOREIGN PATENT DOCUMENTS

| WO | 96/12168 | 4/1996 |

OTHER PUBLICATIONS

Search Report issued Dec. 10, 2007 in priority United Kingdom Patent Application No. 0715659.9.
V. Rosato et al. "Thermodynamic properties of amorphous silicon via tight binding simulation", Computational Materials Science, Jun. 2000.
Simon Duane et al., "Hybrid Monte Carlo", Phys. Lett. B, vol. 195, No. 2, p. 216, Sep. 1987.
B. Mehlig, et al., "Hybrid Monte Carlo method for condensed-matter systems", Physical Review B, vol. 45, No. 2, Jan. 1992.
J. Izaguirre, et al., "Shadow hybrid Monte Carlo: an efficient propagator in phase space of macromolecules", Journal of Computational Physics 200, pp. 581-604Jun. 2004.
G. Benettin, et al., "On the Hamiltonian Interpolation of Near-to-the Identity Symplectic Mappings with Application to Symplectic Integration Algorithms", Journal of Statistical Physics, vol. 74, Nos. 5/6, pp. 1117-1143 (1994).
E. Hairer and C. Lubich, "The life-span of backward error analysis for numerical integrators", Numer. Math., pp. 441-462, (1997).
S. Reich, SIAM, J. Numer. Anal., vol. 36, No. 5, pp. 1549-1570, 475 (1999).
B. Leimkuhler and S. Reich, "Geometric integrators", Simulating Hamiltonian Dynamics (Cambridge University Press, Cambridge, 2005).
E. Hairer, C. Lubich, and G. Wanner, "Chapter VI. Symplectic Integration of Hamiltonian Systems", Geometric Numerical Integration (Springer-Verlag, Berlin Heidelberg, 2002).
B. Moore and S. Reich, "Backward error analysis for multi-symplectic integration methods", Numer. Math. 95, pp. 625-652 (2003).
R. Skeel and D. Hardy, "Practical Construction of Modified Hamiltonians", SIAM, J. Sci. Comput., vol. 23, No. 4, pp. 1172-1188, (2001).
C. Sweet, S. Hampton, and J. Izaguirre, "Optimal implementation of the Shadow Hybrid Monte Carlo method", Tech. Rep. TR-2006-09, University of Notre Dame (Jul. 2006).
C. Sweet, S. Hampton, R. Skeel, and J. Izaguirre, "Separable shadow hybrid Monte Carlo method", Department of Computer Science Engineering, University of Notre Dame (Dec. 2006).
E. Akhmatskaya and S. Reich, "The Targeted Shadowing Hybrid Monte Carlo (TSHMC) Method", pp. 141-153, (2006).
A. Horowitz, "A generalized guided Monte Carlo algorithm", Phys. Lett. B 268, pp. 247-252 (1991).
A. Kennedy and B. Pendleton, Cost of the generalized hybrid Monte Carlo algorithm for free field theory, Nucl. Phys. B 607, pp. 456-510 (2001).

(Continued)

*Primary Examiner* — Michael Borin
(74) *Attorney, Agent, or Firm* — Staas & Halsey LLP

(57) ABSTRACT

A method of simulating behaviour of a molecular system with m degrees of freedom over time comprising a partial momentum refreshment step and a molecular dynamics step, wherein the partial momentum refreshment step comprises: given a starting position q and a starting momentum p of the molecular system, partially refreshing the momentum to define refreshed momentum p' evaluating the shadow Hamiltonian $\mathcal{H}331_{\Delta t}$ at position q and momentum p'; and accepting or rejecting the refreshed momentum p' according to a Metropolis-type function and if p' is accepted using p' as the resulting momentum p and starting position q as the resulting position q or if it is rejected, using p as the resulting momentum p and starting position q as the resulting position; and wherein the molecular dynamics step comprises: given a starting position q and starting momentum p of the molecular system, running a molecular dynamics simulation over a fixed number of iterations and obtaining new position q' and new momentum p'; evaluating the shadow Hamiltonian $\mathcal{H}332_{\Delta t}$ at position q' and momentum p' after the molecular dynamics simulation; and accepting or rejecting the new system configuration produced by the molecular dynamics simulation according to a Metropolis-type function and, if the new system configuration is accepted, using q' as the resulting position q and p' as the resulting momentum p or, if it is rejected, using the original starting position q as the resulting position q and negating the original starting momentum p to give the resulting momentum p; wherein either the partial momentum refreshment or the molecular dynamics step is the first step of the method, and the resulting position and resulting momentum of the first step provides the starting position q and starting momentum p for the next step.

40 Claims, 8 Drawing Sheets

OTHER PUBLICATIONS

H. Andersen, Molecular dynamics simulations at contstand pressure and/or temperature[a], J. Chem. Phys. 72, pp. 2384-2393 (Feb. 1980).

S. Feller, Y. Zhang, R. Pastor, and B. Brooks, "Constant pressure molecular dynamics simulation: The Langevin piston method", J. Chem. Phys. 103, pp. 4613-4621 (Sep. 1995).

M. Allen and D. Tildesley, "Molecular Dynamics", Computer Simulation of Liquids (Clarendon Press, Oxford, 1987).

R. MacKay, "Some Aspects of the Dynamics and Numerics of Hamiltonian Systems", in the dynamics of numerics and the numerics of dynamics, edited by D. Broom-head and A. Iseries (Clarendon Press, Oxford, 1992), pp. 137-193.

S. Gupta, A. Irbäck, F. Karsch, and B. Pterersson, "The Acceptance Probability in the Hybrid Monte Carlo Method", Phys. Lett. B, vol. 242, No. 3, 4, pp. 437-443 (Jun. 1990).

R. Burden and J. Faires, "Numerical Analysis", Eighth Edition, Brooks/Cole, Oct. 2005.

J. Ryckaert, G. Ciccotti, and H. Berendsen, "Numerical Integration of the Cartesian Equations of Motion of a System with Constraints: Molecular Dynamics of n-Alkanes", J. Comput. Phys. 23, pp. 327-341 (1977).

R. Faller and J. de Pablo, "Constant pressure hybrid Molecular Dynamics-Monte Carlo simulations", J. Chem. Phys., vol. 116, No. 1, pp. 55-59 (Jan. 2002).

A. Brünger, C. Brooks, and M. Karplus, "Stochastic Boundary Conditions for Molecular Dynamics Simulations of ST2 Water", Chem. Phys. Lett., vol. 105, No. 5, (Mar. 1984).

H. Berendsen, J. Postma, W. van Gunsteren, A. DiNola, and J. Haak, "Molecular dynamics with coupling to an external bath", J. Chem. Phys., vol. 81, No. 8, pp. 3684-3690 (Oct. 1984).

H. Berendsen, J. Postma, W. van Gunsteren, and J. Hermans, "Interaction Models for Water in Relation to Protein Hydration", in Intermolecular Forces, edited by B. Pullman (D. Reidel Publishing Company, Dordrecht, 1981), pp. 331-342.

E. Lindahl, B. Hess, and D. Spoel, "GROMACS 3.0: a package for molecular simulation and trajectory analysis", J. Mol. Modeling 7, pp. 306-317, (2001).

T. Darden, D. York, and L. Pedersen, "Particle mesh Ewald: An $N \cdot \log(N)$ method for Ewald sums in large systems", J. Chem. Phys., vol. 98, No. 12, pp. 10089-10092 (Jun. 1993).

U. Essmann, L. Perera, M. L. Berkowitz, T. Darden, H. Lee, and L. G. Pedersen, "A smooth particle mesh Ewald method", J. Chem. Phys., vol. 103, No. 19, pp. -85778593 (Nov. 1995).

W. Humphrey, A. Dalke, and K. Schulten, "VMD: Visual Molecular Dynamics", J. Molec. Graphics, vol. 14, pp. 33-38 (Feb. 1996).

W. Anderson, M. Grütter, S. Remington, L. Weaver, and B. Matthews, "Crystallographic Determination of the Mode of Binding of Oligosaccharides to T4 Bacteriophage Lysozyme: Implications for the Mechanism of Catalysis", J. Mol. Biol, 147, pp. 523-543 (1981).

L. Hardy and A. Poteete, "Reexamination of the Role of $Asp^{20}$ in Catalysis by Bacteriophage T4 Lysozyme[†]", Biochemistry 30, pp. 9457-9463 (1991).

R. Kuroki, L. Weaver, and B. Matthews, A Covalent Enzyme-Substrate Intermediate with Saccharide Distortion in a Mutant T4 Lysozyme, Science, vol. 262, pp. 2030-2033 (Dec. 1993).

R. Kuroki, L. Weaver, and B. Matthews, "Structure-based design of a lysozyme with altered catalytic activity", Nat. Struct. Biol., vol. 2, pp. 1007-1011 (Nov. 1995).

R. Kuroki, L. Weaver, and B. Matthews, "Structural basis of the conversion of T4 lysozyme into a transglycosidase by reengineering the active site", Proc. Natl. Acad. Sci., vol. 96, pp. 8949-8954, (Aug. 1999).

R. Neal, "Monte Carlo Implementation", (Chapter 3) *Bayesian learning for neural networks* (Springer-Verlag, New York, 1996).

J. Liu, "Monte Carlo Strategies in Scientific Computing", (Springer-Verlag, New York, 2001).

METHOD, APPARATUS AND COMPUTER PROGRAM FOR MOLECULAR SIMULATION

FIELD OF THE INVENTION

The present invention relates to methods for molecular simulation. Such methods have practical applications in many fields of material science, chemistry, biochemistry and other disciplines. For example, molecular simulation can be used to show positions of toxins within a membrane or anticipate properties of a bio-molecular system. In fact, molecular modelling methods are now routinely used to investigate the structure, dynamics and thermodynamics of inorganic, biological and polymeric systems. The result of molecular modelling can be used to modify such systems to improve their performance without lengthy trials in the field.

I. PRIOR ART

There are two basic approaches to simulation: the deterministic (regular) approach used, for example in molecular dynamics and the stochastic (random) approach used, for example, in Monte Carlo methods, which explore an energy surface by randomly stepping around the configuration space. Kinetic properties are usually best considered by a deterministic approach, whereas thermodynamic properties can be considered using either the deterministic or stochastic approach. Both methods have certain drawbacks. The Monte Carlo method is sometimes unsuited to complex trials and the step size decreases with system size. Molecular dynamics is subject to problems with temperature and pressure control for NVT and NPT ensembles, moreover the force computations required are expensive, some special techniques are needed to constrain some degrees of freedom and consecutive configurations are very similar.

Some recently developed simulation methods use a combination of both approaches. One rigorous method for performing constant temperature simulations is provided by the hybrid Monte Carlo (HMC) method [1, 2]. The HMC method combines constant energy molecular dynamics simulations with a Metropolis acceptance criterion and a momentum resampling step. It is crucial that the constant energy molecular dynamics simulations are performed with a volume preserving and time-reversible method. The generalized hybrid Monte Carlo (GHMC) method [14, 15] is a development of the HMC method. While the HMC method completely resamples the momentum after each Monte Carlo step, the generalized hybrid Monte Carlo (GHMC) method can be implemented with a partial momentum refreshment step. This property seems desirable for keeping some of the dynamic information throughout the sampling process similar to stochastic Langevin and Brownian dynamics simulations. It is, however, ultimate to the success of the GHMC method that the rejection rate in the molecular dynamics part is kept at a minimum. Otherwise an undesirable Zitterbewegung in the Monte Carlo samples is observed. While both simulations have the advantage of providing a rigorous sampling technique, practical experience shows, however, that the acceptance rate in the molecular dynamics part of HMC and GHMC decreases with the size of the molecular system. In particular, HMC simulations become rather inefficient for large biomolecular simulations. Possible rescues include reduction of step-size or increase of accuracy of the molecular simulations by using a higher-order method. Both approaches increase however the computational cost significantly. A different approach has been considered by Hampton and Izaguirre [3], who suggest to make use of the modified equations analysis available for symplectic time-stepping methods such as the Störmer-Verlet method. The fundamental result of [4-6] is that any symplectic integrator (see [7, 8] for a general discussion of symplectic methods) possesses a modified (or shadow) Hamiltonian $\mathcal{H}_{\Delta t}$, which is preserved along the numerical trajectories up to terms $\propto \exp(-c/\Delta t)$, where $c>0$ is a constant and $\Delta t$ is the step-size. The shadow hybrid Monte Carlo (SHMC) method [3] samples from a properly defined modified energy and is able to achieve very high acceptance rates in the molecular dynamics part of HMC. Efficient algorithms for computing modified energies can be found in [9] and [10]. However, SHMC uses an empirical tuning factor, which is specific to each system and not easy to determine. Moreover, the momentum resampling step becomes more complex under the SHMC method. In fact, the necessary balance between increased acceptance in the molecular dynamics update and reduced acceptance in the momentum updates limits the efficiency gains of SHMC over HMC [11]. More recently, the S2HMC method has been introduced in [12], which overcomes the efficiency limitation of SHMC at the level of fourth-order modified energies. An extension of S2HMC to higher-order modified energies is currently not available.

In a related paper [13], Akhmatskaya and Reich proposed to apply the idea of modified energies to an HMC method with partial momentum updates. The targeted shadow hybrid Monte Carlo (TSHMC) method achieves high acceptance rates in both the molecular dynamics as well as in the momentum refreshment steps. However, it is not derived in generalized co-ordinates and the parameter used in the momentum refreshment step cannot recover the whole range of special cases in a rigorous manner.

It is desirable to provide a method and apparatus for simulation which overcome or at least mitigate some of the disadvantages of the prior art.

The invention is defined in the independent claims, to which reference should now be made. Advantageous embodiments are set out in the sub claims.

According to one preferred embodiment of an aspect of the invention there is provided a method of simulating behaviour of a molecular system with m degrees of freedom over time comprising a partial momentum refreshment step and a molecular dynamics step, wherein the partial momentum refreshment step comprises: given a starting position q and a starting momentum p of the molecular system, partially refreshing the momentum to define refreshed momentum p' using a noise vector u, where:

$$\begin{pmatrix} u' \\ p' \end{pmatrix} = \begin{pmatrix} \cos(\phi) & \sin(\phi) \\ \sin(\phi) & -\cos(\phi) \end{pmatrix} \begin{pmatrix} u \\ p \end{pmatrix}$$

where p', p: refreshed and current momentum, $0 \leq \phi \leq \pi/2$, u', u: new and current noise vectors, $u=\beta^{-1/2}\mathcal{M}(q)^{1/2}\xi$, $\xi_i \sim N(0, 1)$, $i=1, \ldots, m$, $N(0,1)$ denoting the normal distribution with zero mean and unit variance, $\mathcal{M}$: mass matrix, $\beta=1/K_B T$ where T is temperature; evaluating the shadow Hamiltonian $\mathcal{H}_{\Delta t}$ at position q and momentum p'; and accepting or rejecting the refreshed momentum p' according to a Metropolis-type function and if p' is accepted using p' as the resulting momentum p and starting position q as the resulting position q or if it is rejected, using p as the resulting momentum p and starting position q as the resulting position; and wherein the molecular dynamics step comprises: given a starting position q and starting momentum p of the molecular system, running a molecular dynamics simulation over a fixed number of iterations and obtaining new position q' and new momentum p'; evaluating the shadow Hamiltonian $\mathcal{H}_{\Delta t}$ at position q' and momentum p' after the molecular dynamics simulation; and accepting or rejecting the new system configuration produced by the molecular dynamics simulation according to a Metropolis-type function and, if the new system configuration is accepted, using q' as the resulting position q and p' as the resulting momentum p or, if it is rejected, using the original starting position q as the resulting position q and negating the original starting momentum p to give the resulting momentum p; wherein either the partial momentum refreshment or the molecular dynamics step is the first step of the method, and the resulting position and resulting momentum of the first step provides the starting position q and starting momentum p for the next step.

Recently developed techniques have moved away from the generalized coordinates and rigorous sampling in GHMC and its exponential performance degradation with increased system size and time step. Instead, SHMC and TSHMC have adopted the hybrid Monte Carlo principle using a different calculation method and thereby achieved some success in overcoming the disadvantages of HMC and GHMC. Surprisingly, however, the present inventors have found that it is possible to build on the rigorous GHMC principles whilst overcoming the difficulties associated with larger system sizes.

We call the new method of invention embodiments generalized shadow hybrid Monte Carlo (GSHMC). The link to GHMC has allowed us to develop a more efficient momentum refreshment step for GSHMC. This partial momentum update keeps some of the dynamic information throughout the sampling process similar to stochastic Langevin and Brownian dynamics simulations. Furthermore, we develop the GSHMC method for molecular systems in generalized coordinates and for the constant pressure formulation of Andersen [16] in particular. A key factor is the derivation of an appropriate symplectic and time-reversible time-stepping method and the formulation of modified energies. As for GHMC methods, a high acceptance rate in the molecular dynamics part of GSHMC is necessary to avoid an undesirable Zitterbewegung due to momentum reversal after a rejected molecular dynamics update. Under the GSHMC method we can achieve this by using modified energies of high enough order.

One particular preferred aspect is the introduction of a multiple partial momentum refreshment step, which repeats the entire partial momentum refreshment step a selected number of times consecutively, to provide a final resulting momentum. The multiple step effectively chooses the best option from the selected number of partial momentum steps. This simple modification to the method allows improvement of the acceptance rate in the subsequent metropolis function, (which is an adaptation of the classical metropolis function) and at relatively low cost in terms of processing power and/or time.

Equally, it might give faster convergence to start the method with the partial momentum refreshment step rather than the molecular dynamics iterations. The entire method may be repeated a selected number of times or until a preferred result in terms of system energy or stability is achieved.

Because of its formulation, GSHMC can be used for sampling without preserving dynamic information or for statistically rigorous stochastic Langevin molecular dynamics.

The result of the simulation can be further improved by using a change of variable for the momentum p. The modified value is a function of position and momentum over time which increases the acceptance rate of the partial momentum refreshment step.

Advantageously the method in the molecular dynamics step can use the generalised or standard Störmer-Verlet method. This facilitates widespread use of the GSHMC method.

Since the method uses shadow Hamiltonians, reference system energy calculations which are asymptotic expansions of the true Hamiltonian in powers of step size $\Delta t$, some re-weighting is needed for high accuracy. The shadow Hamiltonian is a more sensitive indicator than the true Hamiltonian of drift in the energy caused by instability, in that it can eliminate some of the noise in true Hamiltonian values. Nevertheless for accurate results, re-weighting of the calculated properties of the system is needed at the end of the method.

GSHMC is applicable to various ensembles and has been explicitly derived for NVT ensembles and NPT ensembles. This makes it particularly suitable for biomolecular simulation and/or material sciences simulation.

The method is preferably carried out by a computer, the specification and arrangement of such a computer being well known to a person skilled in the art of molecular simulation.

There is also a more generalized application for the simulation described in detail for molecular simulation in the following. GSHMC can be used to solve statistical inference problems in the same way that the HMC method has already been applied. In such methods, the function defined and linked to Hamiltonian energy is V, a user defined cost function and the associated dynamics in q and p is of conservative Newtonian form. Here, q is a position, parameter or configuration of the system, p is the momentum and M is from mass matrix.

The detailed description is organized as follows. We first summarize the GHMC method. We then show how to derive a symplectic and time-reversible time-stepping method for constant energy molecular dynamics in generalized coordinates. This is followed by the introduction of the GSHMC method, the derivation of a fourth-order modified energy, and the discussion of improved momentum refreshment steps. We provide implementation details for GSHMC simulations under an NVT and NPT ensemble. We demonstrate that the constant pressure GSHMC method can be thought of as a rigorous implementation (in the sense of time-stepping artefacts) of the Langevin piston method of Feller et al. [17]. We finally provide numerical results from simulations for argon and a lysozyme protein (2LZM) in water solvent and demonstrate the superiority and sampling efficiency of GSHMC over the prior art simulation methods.

II. THE GENERALIZED HYBRID MONTE CARLO METHOD

We consider a molecular system with m degrees of freedom described by generalized coordinates $q \in \mathbb{R}^m$, potential energy function V(q) and symmetric (possibly non-constant) mass matrix $\mathcal{M}(q) \in \mathbb{R}^{m \times m}$. The term q can be seen as a collection of atomic positions in the molecular system and m represents the degrees of freedom. The corresponding equations of motion can be derived from the Lagrangian functional $$L[q] = \int_{t_0}^{t_1} \mathcal{L}(\dot{q}(t), q(t)) dt \tag{1}$$

with Lagrangian density $$\mathcal{L}(\dot{q}, q) = \frac{1}{2}\dot{q} \cdot [\mathcal{M}(q)\dot{q}] - V(q). \quad (2)$$

The associated Euler-Lagrange equations are given by $$\frac{d}{dt}\frac{\partial \mathcal{L}}{\partial \dot{q}} - \frac{\partial \mathcal{L}}{\partial q} = \frac{d}{dt}[\mathcal{M}(q)\dot{q}] + \nabla_q V(q) - \frac{1}{2}\nabla_q\{\dot{q} \cdot [\mathcal{M}(q)\dot{q}]\} = 0. \quad (3)$$

To switch to the Hamiltonian formulation, we first introduce the momentum conjugate to q (which can be seen as a collection of atomic momenta in the molecular system);

$$p = \frac{\partial \mathcal{L}}{\partial \dot{q}} = \mathcal{M}(q)\dot{q}. \quad (4)$$

The resulting Hamiltonian (energy) is $$\mathcal{H}(q, p) = \frac{\partial \mathcal{L}}{\partial \dot{q}} \cdot \dot{q} - \mathcal{L} = \frac{1}{2}\dot{q} \cdot [\mathcal{M}(q)\dot{q}] + V(q) = \frac{1}{2}p \cdot [\mathcal{M}(q)^{-1}p] + V(q) \quad (5)$$

with canonical equations of motion $$\dot{q} = +\nabla_p \mathcal{H}(q, p) = \mathcal{M}(q)^{-1}p, \quad (6)$$

$$\dot{p} = -\nabla_p \mathcal{H}(q, p) = -\frac{1}{2}\nabla_q\{p \cdot [\mathcal{M}(q)^{-1}p]\} - \nabla_q V(q). \quad (7)$$

We now recall that a Markov process will converge to some distribution of configurations if it is constructed out of updates each of which has the desired distribution as a fixed point, and which taken together are ergodic. The generalized hybrid Monte Carlo (GHMC) algorithm for sampling from the canonical ensemble with density function $$\rho(q,p) \propto \exp(-\beta \mathcal{H}(q,p)), \quad (8)$$

$\beta=1/K_B T$, is defined as the concatenation of a molecular dynamics Monte Carlo (MDMC) and a partial momentum refreshment Monte Carlo (PMMC) step [14, 15]. We now describe both steps in more detail.

A. Molecular Dynamics Monte Carlo (MDMC)
This step in turn consists of three parts:
(i) Molecular dynamics (MD): an approximate integration of Hamilton's equations of motion (6)-(7) with a time-reversible and volume-preserving method $\psi_{\Delta t}$ over L steps and step-size $\Delta t$. We will derive an appropriate numerical time-stepping method in section III.
The resulting time-reversible and volume-preserving map from the initial to the final state is denoted by $U_{96}$: $(q,p) \rightarrow (q',p')$, $\tau=L\Delta t$. Recall that a map $U_\tau$ is called time-reversible if $U_\tau = U_{-\tau}^{-1}$ and volume-preserving if $$\det \frac{\partial(q', p')}{\partial(q, p)} = 1.$$

(ii) A momentum flip $\mathcal{F}$: (q,p)→(q,−p).

(iii) Monte Carlo (MC): a Metropolis accept/reject test $$(q', p') = \begin{cases} \mathcal{F} \cdot U_T(q, p) & \text{with probability min}(1, \exp(-\beta\delta H)) \\ (q, p) & \text{otherwise} \end{cases} \quad (9)$$

with $$\delta H := \mathcal{H}(U_\tau(q,p)) - \mathcal{H}(q,p) = \mathcal{H}(\mathcal{F} \cdot U_\tau(q,p)) - \mathcal{H}(q,p) \quad (10)$$

and $\mathcal{H}$ defined by (5)

Molecular dynamics Monte Carlo (MDMC) satisfies detailed balance since $(\mathcal{F} \cdot U_\tau)^2 = \text{id}$ and $U_\tau$ is volume conserving.

B. Partial Momentum Refreshment Monte Carlo (PMMC)

We first apply an extra momentum flip $\mathcal{F}$ so that the trajectory is reversed upon an MDMC rejection (instead of upon an acceptance). The momenta p are now mixed with a normal (Gaussian) i.i.d. distributed noise vector $u \in \mathbb{R}^m$ and the complete partial momentum refreshment step is given by $$\begin{pmatrix} u' \\ p' \end{pmatrix} = \begin{pmatrix} \cos(\phi) & -\sin(\phi) \\ \sin(\phi) & \cos(\phi) \end{pmatrix} \cdot \mathcal{F}\begin{pmatrix} u \\ p \end{pmatrix} \quad (11)$$

where $$u = \beta^{-1/2}\mathcal{M}(q)^{1/2}\xi, \xi = (\xi_1, \ldots, \xi_m)^T, \xi_i \sim N(0,1),$$
$$i = 1, \ldots, m, \quad (12)$$

and $0 \leq \phi \leq \pi/2$. Here $N(0,1)$ denotes the normal distribution with zero mean and unit variance.

If p and u are both distributed according to the same normal (Gaussian) distribution, then so are p' and u'. This special property of Gaussian random variables under an orthogonal transformation (11) makes it possible to conduct the partial momentum refreshment step without a Metropolis accept/reject test. See [15] for details.

C. Special Cases of GHMC
Several well-known algorithms are special cases of GHMC:
The standard hybrid Monte Carlo (HMC) algorithm of Duane, Kennedy, Pendleton and Roweth [1] is the special case where $\phi=\pi/2$. The momentum flips may be ignored in this case since p'=u in (11) and the previous value of p is entirely discarded. According to theoretical results in [15], this choice is optimal for sampling purposes and long MD trajectories. However, one has to keep in mind that the theoretical setting of [15] is unlikely to apply for biomolecular simulations and that a different choice of could be more appropriate for such simulations.
The choice $\phi=0$ corresponds to constant energy molecular dynamics under the assumption that the propagator $U_\tau$ conserves energy exactly.
The Langevin Monte Carlo algorithm of Horowitz [14] corresponds to L=1; i.e., a single MD time-step with T=$\Delta t$, and $\phi$ arbitrary. The single step (L=1) may be replaced by a small number of MD steps and $\tau=L\Delta t$. Langevin Monte Carlo recovers stochastic Langevin molecular dynamics [18]

$$\dot{q} = \mathcal{M}^{-1}(q)p, \quad (13)$$

$$\dot{p} = -\frac{1}{2}\nabla_q\{p \cdot [\mathcal{M}(q)^{-1}p]\} - \nabla_q V(q) - \gamma p + \sigma \dot{W}.$$

provided $\phi = \sqrt{2\gamma\tau} \ll 1$. Here, $\gamma > 0$ is a constant, $W(t)$ is an m-dimensional Wiener process, and $a$ is determined by the standard fluctuation-dissipation relation [18]. Indeed, we find that (11) without the momentum flip $\mathcal{F}$ reduces to $$p' \approx (1-\gamma\tau)p + (2\gamma\tau)^{1/2}u \qquad (14)$$

for $\phi = \sqrt{2\gamma\tau} \ll 1$ and one may view the GHMC algorithm as a mean to perform stochastic molecular dynamics (instead of using GHMC as a pure sampling device).

III. A SYMPLECTIC AND TIME-REVERSIBLE PROPAGATOR

To implement the generalized hybrid Monte Carlo method for Hamiltonian systems of the form (6)-(7), we need to find a time-reversible and volume-preserving approximation to the exact solution flow map. The essential idea is to replace exact time derivatives $\dot{q}$ in the Lagrangian density (2) by (forward and backward) finite difference approximations $$\delta_t^+ q^n = \frac{q^{n+1}-q^n}{\Delta t}, \; \delta_t^- q^n = \frac{q^n - q^{n-1}}{\Delta t}, \qquad (15)$$

and to start from a discrete approximation $$L_{\Delta t}[\{q^n\}] = \sum_n \mathcal{L}_{\Delta t}(\delta_t^+ q^n, \delta_t^- q^n, q^n)\Delta t \qquad (16)$$

to the Lagrangian functional (1) with $$\mathcal{L}_{\Delta t}(\delta_t^+ q^n, \delta_t^- q^n, q^n) = \frac{1}{4}\left\{\begin{array}{l} \delta_t^+ q^n \cdot [\mathcal{M}(q^n)\delta_t^+ q^n] + \\ \delta_t^+ q^n \cdot [\mathcal{M}(q^n)\delta_t^- q^n] \end{array}\right\} - V(q^n). \qquad (17)$$

Following the discrete variational principle (see, e.g., [8]), we find the associated discrete equations of motion from $\delta L_{\Delta t}/\delta q^n = 0$ and obtain the generalized leapfrog scheme $$0 = \delta_t^+\left\{\frac{1}{2}[\mathcal{M}(q^n) + \mathcal{M}(q^{n-1})]\delta_t^- q^n\right\} + \qquad (18)$$
$$\nabla_q V(q^n) - \frac{1}{4}\nabla_q \left\{\begin{array}{l}\delta_t^+ q^n \cdot [\mathcal{M}(q^n)\delta_t^+ q^n] + \\ \delta_t^- q^n \cdot [\mathcal{M}(q^n)\delta_t^- q^n]\end{array}\right\}.$$

This scheme is time-reversible since replacing $q^{n+1}$ by $q^{n-1}$ and $\Delta t$ by $-\Delta t$ leaves the scheme unchanged.

We now convert this scheme into an equivalent (in terms of q-propagation) symplectic one-step method by noting that $$\sum_n \mathcal{L}_{\Delta t}(\delta_t^+ q^n, \delta_t^- q^n, q^n)\Delta t = \sum_n \mathcal{L}_{\Delta t}^{n+1/2} \text{ with} \qquad (19)$$

$$\mathcal{L}_{\Delta t}^{n+1/2} = \frac{1}{2}\left\{\begin{array}{l}\delta_t^+ q^n \cdot [\mathcal{M}(q^n) + \mathcal{M}(q^{n+1})]\delta_t^+ q^n - \\ [V(q^n) + V(q^{n+1})]\end{array}\right\}\Delta t. \qquad (20)$$

The discrete approximation $\mathcal{L}_{\Delta t}^{n+1/2}$ is now used as a generating function (see, e.g., [8]) to yield a symplectic (and hence volume-preserving) time stepping method $$\Psi_{\Delta t}: (q^n, p^n) \to (q^{n+1}, p^{n+1}) \text{ via} \qquad (21)$$

$$p^{n+1} = +\nabla_{q^{n+1}} \mathcal{L}_{\Delta t}^{n+1/2} \qquad (22)$$
$$= \frac{1}{2}(\mathcal{M}(q^n) + \mathcal{M}(q^{n+1}))\delta_t^+ q^n +$$
$$\frac{\Delta t}{2}\nabla_q\{\delta_t^+ q^n \cdot [\mathcal{M}(q^{n+1})\delta_t^+ q^n] - V(q^{n+1})\} \text{ and}$$

$$p^n = -\nabla_{q^n} \mathcal{L}_{\Delta t}^{n+1/2} \qquad (23)$$
$$= \frac{1}{2}(\mathcal{M}(q^n) + \mathcal{M}(q^{n+1}))\delta_t^+ q^n -$$
$$\frac{\Delta t}{2}\nabla_q\{\delta_t^+ q^n \cdot [\mathcal{M}(q^n)\delta_t^+ q^n] - V(q^n)\}.$$

Given $(q^n, p^n)$, the map $\psi_{\Delta t}$ is implemented numerically by first solving (23) for $q^{n+1}$. The new momentum $p^{n+1}$ is then given explicitly by (22). We finally note that the generating function (20) was first proposed by MacKay in [19] for deriving symplectic methods for systems with general Lagrangian density $L(\dot{q},q)$.

The generalized Störmer-Verlet method is second-order in time and the average energy fluctuation $\langle \delta \mathcal{H} \rangle$ satisfies $$\langle \delta \mathcal{H} \rangle = \mathcal{O}(m\Delta t^4), \qquad (24)$$

where m is the number of degrees of freedom and $\delta \mathcal{H}$ is given by (10) [3, 20]. Following the analysis of [14, 20], the average Metropolis acceptance rate for the MDMC step is given by $$P_{acc} = \text{erfc}\left(\frac{1}{2}\sqrt{\beta\langle\delta\mathcal{H}\rangle}\right) \qquad (25)$$

and the acceptance rate deteriorates with increasing system size m.

IV. GENERALIZED SHADOW HYBRID MONTE CARLO (GSHMC) METHOD

The basic idea of the GSHMC method is to implement the GHMC method with respect to an appropriately modified reference energy $\mathcal{H}_{\Delta t}$. This reference energy is chosen such that the acceptance rate that we have derived as (25) for shadow Hamiltonian systems in the MDMC part of the GHMC algorithm is increased. This goal can indeed be achieved by making use of backward error analysis and the implied existence of modified energies, which are preserved to high accuracy by the time-stepping method [3, 13]. The price we pay for this increased acceptance rate is that (i) the PMMC step becomes more complex and that (ii) computed samples need to be re-weighted after the simulation to become exactly consistent with the desired canonical distribution function (8).

We provide the details of the GSHMC method in several steps. First we describe the MDMC step when implemented with respect to a reference energy $\mathcal{H}_{\Delta t} = \mathcal{H} + \mathcal{O}(\Delta t^p)$, $p \geq 4$. This step is a minor but important modification of the GHMC method. We then explicitly derive a fourth-order modified energy $\mathcal{H}_{\Delta t}^{[4]}$ for the generalized Störmer-Verlet method of Section III. We finally discuss the necessary modifications to the momentum refreshment Monte Carlo step, which are vital to the success of the GSHMC method.

A. Modified MDMC Step

The MDMC step of Section II A remains as before with only (10) replaced by $$\delta H = \mathcal{H}_{\Delta t}(U_\tau(q,p)) - \mathcal{H}_{\Delta t}(q,p). \qquad (26)$$

In the remaining part of the subsection we derive a fourth-order reference energy $\mathcal{H}_{\Delta t} = \mathcal{H}_{\Delta t}^{[4]}$ for the generalized Störmer-Verlet method of Section III. A generalization to sixth-order and higher can be found in the Appendix.

Given the numerical trajectory $\{q^n\}_{n=-k}^{L+k}$, we construct to $t_n$, $n \in \{0,L\}$, an interpolation polynomial $Q(t) \in \mathbb{R}^m$ of order $p \leq 2k$, $k \geq 2$, such that $$Q(t_i) = q^i, \quad i = n-k, \ldots, n, \ldots, n+k \qquad (27)$$

"[21] We make use of standard Taylor expansion, i.e.

$$q^{n\pm 1} = Q(t_n) \pm \Delta t \dot{Q}(t_n) + \frac{\Delta t^2}{2}\ddot{Q}(t_n) \pm \frac{\Delta t^3}{6}Q^{(3)}(t_n) + \ldots, \qquad (28)$$

in the discrete Lagrangian density (17) to obtain $$\mathcal{L}_{\Delta t} = \frac{1}{4}\left(\dot{Q} + \frac{\Delta t}{2}\ddot{Q} + \frac{\Delta t^2}{6}Q^{(3)}\right) \cdot \left[\mathcal{M}(Q)\left(\dot{Q} + \frac{\Delta t}{2}\ddot{Q} + \frac{\Delta t^2}{6}Q^{(3)}\right)\right] + \qquad (29)$$

$$\frac{1}{4}\left(\dot{Q} - \frac{\Delta t}{2}\ddot{Q} + \frac{\Delta t^2}{6}Q^{(3)}\right) \cdot \left[\mathcal{M}(Q)\left(\dot{Q} - \frac{\Delta t}{2}\ddot{Q} + \frac{\Delta t^2}{6}Q^{(3)}\right)\right] -$$

$$V(Q) + O(\Delta t^3)$$

$$= \mathcal{L}(\dot{Q}, Q) + \Delta t^2 \delta \mathcal{L}^{[4]}(Q^{(3)}, \ddot{Q}, \dot{Q}, Q) + O(\Delta t^4) \text{ with}$$

$$\delta \mathcal{L}^{[4]}(Q^{(3)}, \ddot{Q}, \dot{Q}, Q) = \frac{1}{24}\{3\ddot{Q} \cdot [\mathcal{M}(Q)\ddot{Q}] + 4\dot{Q} \cdot [\mathcal{M}(Q)Q^{(3)}]\} \qquad (30)$$

and with all quantities involving the interpolation polynomial $Q(t)$ evaluated at $t = t_n$.

We note that the truncated expansion $$\mathcal{L}_{\Delta t}^{[4]} = \frac{1}{2}\dot{Q} \cdot [\mathcal{M}(Q)\dot{Q}] - V(Q) + \frac{\Delta t^2}{24}\left\{\begin{array}{c}3\ddot{Q} \cdot [\mathcal{M}(Q)\ddot{Q}] + \\ 4\dot{Q} \cdot [\mathcal{M}(Q)Q^{(3)}]\end{array}\right\} \qquad (31)$$

Can be viewed as a new (higher-order) Lagrangian density with associated (higher-order) Euler-Lagrange equations. We derive the associated conversed energy according to the formula $$\mathcal{H}_{\Delta t}^{[4]} = \frac{\partial \mathcal{L}_{\Delta t}^{[4]}}{\partial \dot{Q}} \cdot \dot{Q} + \frac{\partial \mathcal{L}_{\Delta t}^{[4]}}{\partial \ddot{Q}} \cdot \ddot{Q} - \frac{d}{dt}\frac{\mathcal{L}_{\Delta t}^{[4]}}{\partial \ddot{Q}} \cdot \dot{Q} + \qquad (32)$$

$$\frac{\partial \mathcal{L}_{\Delta t}^{[4]}}{\partial Q^{(3)}} \cdot Q^{(3)} - \frac{d}{dt}\frac{\partial \mathcal{L}_{\Delta t}^{[4]}}{\partial Q^{(3)}} \cdot \ddot{Q} + \frac{d^2}{dt^2}\frac{\partial \mathcal{L}_{\Delta t}^{[4]}}{\partial Q^{(3)}} \cdot \dot{Q} - \mathcal{L}_{\Delta t}^{[4]}.$$

An explicit expression is provided by $$\mathcal{H}_{\Delta t}^{[4]} = \frac{1}{2}\dot{Q} \cdot [\mathcal{M}(Q)\dot{Q}] + V(Q) + \frac{\Delta t^2}{24} \qquad (33)$$

$$\left\{4\dot{Q} \cdot [\mathcal{M}(Q)Q^{(3)}] - 6\dot{Q} \cdot \frac{d}{dt}[\mathcal{M}(Q)\ddot{Q}] + 4\dot{Q} \cdot \frac{d^2}{dt^2}[\mathcal{M}(Q)\dot{Q}]\right\} +$$

$$\frac{\Delta t^2}{24}\left\{3\ddot{Q} \cdot \mathcal{M}(Q)\ddot{Q} - 4\ddot{Q} \cdot \frac{d}{dt}[\mathcal{M}(Q)\dot{Q}]\right\}.$$

It can be shown that $\mathcal{H}_{\Delta t}^{[4]}$ is preserved to fourth-order along trajectories of (23)-(22) and (18), respectively, provided $k=2$ and $p=4$ in (27). This procedure can be generalized and we obtain modified energies $\mathcal{H}_{\Delta t}^{[2k]}$ for any $k \geq 2$. See the Appendix for the case $k=3$. These modified energies $\mathcal{H}_{\Delta t}^{[2k]}$, with an appropriate order $p=2k \geq 4$, will be used in the GSHMC method as the reference energy function $\mathcal{H}_{\Delta t}$.

Using the modified energies, the estimate (24) gets replaced by $$\langle \delta \mathcal{H} \rangle = O(m\Delta t^{4k}), \qquad (34)$$

with $\delta \mathcal{H}$ now being given by (26) and $\mathcal{H}_{\Delta t} = \mathcal{H}_{\Delta t}^{[2k]}$. Hence an increase in system size m can be counterbalanced by an increase in the order of the modified energy to keep the product of m and

B. Modified PMMC Step

To give a comparison with other recently developed simulation technologies, the original THSMC method has been based on a simple momentum proposal step of the form with an arbitrary parameter, which can be disadvantageous because it is not known what kind of dynamics is can be recovered.

$$p' = p + \sigma u. \qquad (35)$$

Here $\sigma > 0$ is the free parameter and u is defined by (12). Smaller values of $\sigma$ lead to smaller perturbations in the momenta. The new set of momenta p' is accepted/rejected according to an appropriate Metropolis criterion [13].

It has been found that increased values of $\sigma$ lead to an increased rejection rate. In this section, a modified momentum update is proposed for GSHMC to reduce such an undesirable increase in the rejection rate. This modification is indeed found to significantly improves the efficiency of GSHMC as a sampling tool.

The idea of the modification is to combine the GHMC momentum update (11) with the fact that in GSHMC one samples with respect to a modified energy function $\mathcal{H}_{\Delta t}$. This idea can be realized by implementing the PMMC step of Section IIB as a Markov chain Monte Carlo step with respect to the reference energy $\mathcal{H}_{\Delta t}$. Specifically, we define u as in (12) and propose a new set of momenta p' and auxiliary variables u' by (11). The set of momenta p' and the vector u' are accepted according to the Metropolis test $$(u', p') = \begin{cases} [R(\phi)(u, p)^T]^T & \text{with probability } P(q, p, u, p', u') \\ (u, p) & \text{otherwise} \end{cases}, \qquad (36)$$

where $$P(q, p, u, p', u') = \qquad (37)$$

$$\min\left(1, \frac{\exp\left(-\beta\left[\mathcal{H}_{\Delta t}(q, p') + \frac{1}{2}(u')^T \mathcal{M}(q)^{-1} u'\right]\right)}{\exp\left(-\beta\left[\mathcal{H}_{\Delta t}(q, p) + \frac{1}{2}u^T \mathcal{M}(q)^{-1} u\right]\right)}\right) \text{ and}$$

$$R(\phi) = \begin{bmatrix} \cos(\phi) & \sin(\phi) \\ \sin(\phi) & -\cos(\phi) \end{bmatrix}. \qquad (38)$$

It should be noted that the updated variable u' is entirely discarded after each momentum refreshment step and is replaced by a new set of random variables (12). The Monte Carlo step is therefore best understood by interpreting the update as a 'classical' hybrid Monte Carlo method with u taking the role of 'momentum' and p the role of 'positions'. Note that the 'real' positions q are not changed. Note furthermore that (11) is a linear map from (p, u) to (p',u'). This map is characterized by the 2×2 matrix (38). Since det(R)=−1 and $R^2 = I$, the proposal step (11) satisfies detailed balance. Hence

(12) and (11) together with (36) sample from a canonical distribution with density function $$\rho_{ext}(q, p, u) \propto \exp\left(-\beta\left[\mathcal{H}_{\Delta t}(q, p) + \frac{1}{2}u^T \mathcal{M}(q)^{-1} u\right]\right). \quad (39)$$

The angle $\phi$ in (38) is chosen such that the rejection rate in the momentum refreshment step is below 10%. A much higher rejection rate would imply that the system gets 'thermalized' too infrequently. A fixed rejection rate implies that larger systems require a smaller value of $\phi$, which seems acceptable once we take into account that large NVE simulations behave almost like an NVT ensemble.

To further decrease the rejection rate one can repeat the refreshment step before continuing with the molecular dynamics part of GSHMC. Hence the complete GSHMC cycle consists then of a molecular dynamics Monte Carlo step, a momentum flip, a Monte Carlo momentum refreshment step, followed by another Monte Carlo momentum refreshment step. In other words, GSHMC becomes the concatenation of four Markov processes (here we counted the momentum flip as an independent Markov process) with identical invariant distribution functions (here the canonical distribution with respect to a modified Hamiltonian $\mathcal{H}_{\Delta t}$). Of course, this approach can be further modified by additional (relatively inexpensive) momentum update steps.

Inspired by the work of Sweet et al. [12], we finally mention an additional strategy for increasing the acceptance rate of the PMMC step. We replace (11) by $$\begin{pmatrix} u' \\ \bar{p}' \end{pmatrix} = \begin{pmatrix} \cos(\phi) & \sin(\phi) \\ \sin(\phi) & -\cos(\phi) \end{pmatrix} \begin{pmatrix} u \\ \bar{p} \end{pmatrix}, \quad (40)$$

where $\bar{p}'$ is defined through an appropriate change of variables $\bar{p}=\psi(q,p,\Delta t)$. It is assumed that the map $\psi$ is invertible in the momentum vector p. The new momentum vector p', implicitly defined by $\bar{p}'=\psi(q,p',\Delta t)$, is then accepted with probability (37).

See [12] for an appropriate choice of $\psi$ in case of a constant mass matrix. More specifically, given (q,p), we perform a single time step forward and backward in time. The results are denoted by $(q^+,p^+)$ and $(q^-,p^-)$, respectively. We define $$\bar{p} = \psi(q, p, \Delta t) := p - \frac{\Delta t}{24}\left(\nabla_q V(q^+) - \nabla_q V(q^-)\right). \quad (41)$$

Note that, contrary to the S2HMC method [12], the modified PMMC step (40)-(41) can be used together with any choice of the reference Hamiltonian $\mathcal{H}_{\Delta t}$ in (37) and also for systems with non-constant mass matrix.

C. Reweighting

Given an observable $\Omega(q,p)$ and its values $\Omega_i$, $i=1,\ldots,K$, along a sequence of states $(q_i,p_i)$, $i=1,\ldots,K$, computed by the GSHMC method, we need to reweight $\Omega_i$ to compute averages $\langle\Omega\rangle_K$ according to the desired canonical distribution (8). In particular, one needs to apply the formula $$\langle\Omega\rangle_K = \frac{\sum_{i=1}^{K} w_i \Omega_i}{\sum_{i=1}^{K} w_i} \quad (42)$$

with $$w_i = \exp(-\beta\{\mathcal{H}(q_i,p_i) - \mathcal{H}_{\Delta t}(q_i,p_i)\}). \quad (43)$$

APPLICATIONS

A. Constant Temperature and Volume (NVT) GSHMC

The starting point of any (classical) molecular simulation is a system of N particles, which interact through both long and short range forces via Newton's second law. We write the equations of motion in the form $$\dot{r} = M^{-1} p_r, \quad \dot{p}_r = -\nabla_r V(r), \quad (44)$$

where $r \in \mathbb{R}^{m3N}$ is the vector of atomic positions, $p_r \in \mathbb{R}^{m3N}$ the associated momentum vector. $M \in \mathbb{R}^{m3N \times 3N}$ is the (constant) symmetric mass matrix and $V: \mathbb{R}^{m3N} \to \mathbb{R}^m$ is the empirical potential energy function. The equations of motion (44) are equivalent to the Euler-Lagrange equations $$M\ddot{r} + \nabla_r V(r) = 0 \quad (45)$$

for the Lagrangian density $$\mathcal{L} = \frac{1}{2}\dot{r} \cdot [M\dot{r}] - V(r). \quad (46)$$

We find that (46) fits into the general form (2) with constant mass matrix $\mathcal{M}(q)=M$, $q=r$, and $m=3N$.

Because the mass matrix M is now constant, the symplectic time-stepping method $\psi_{\Delta t}$, defined by (22)-(23) becomes equivalent to the standard Störmer-Verlet method (see, e.g., [7, 8])

$$p_r^{n+1/2} = p_r^n - \frac{\Delta t}{2}\nabla_r V(r^n), \quad (47)$$

$$r^{n+1} = r^n + M^{-1} p_r^{n+1/2}, \quad (48)$$

$$p_r^{n+1} = p_r^{n+1/2} - \frac{\Delta t}{2}\nabla_r V(r^{n+1}), \quad (49)$$

and the expression for the modified energy $\mathcal{H}_{\Delta t}^{[4]}$ reduces to $$\mathcal{H}_{\Delta t}^{[4]} = \frac{1}{2}\dot{R} \cdot [M\dot{R}] + V(R) + \frac{\Delta t^2}{24}\{2\dot{R} \cdot [MR^{(3)}] - \ddot{R} \cdot M\ddot{R}\}, \quad (50)$$

where R(t) denotes now the interpolating polynomial and replaces Q(t) in (33).

The application of the GSHMC method, as described in Section IV, is now straightforward. Numerical results will be presented in Section VII.

We finally note that the equations of motion (45) subject to holonomic constraints (such as bond stretching and bending constraints) can be treated numerically by the SHAKE extension [22] of the standard Störmer-Verlet/leapfrog method. The associated modified energies remain unaffected by that extension and the fourth-order modified energy, in particular, is still provided by the expression (50).

B. Constant Temperature and Pressure (NPT) GSHMC

We first summarize the constant energy and pressure formulation of Andersen [16]. We then discuss a symplectic and time-reversible integration method and derive its fourth-order modified energy. This provides the essential building block to extend the GSHMC method to molecular simulations in an NPT ensemble.

1. Constant Pressure Molecular Dynamics

Given a classical molecular system described by 44), the constant pressure and energy (NPE) formulation of Andersen is derived as follows. The coordinate vector $r \in \mathbb{R}^{m3N}$ in (45) is replaced by a scaled vector $d \in \mathbb{R}^{m3N}$ defined by $$d = r/V^{1/3} \quad (51)$$

where $V$ is the volume of the simulation box. Consider now the extended Langragian density $$\mathcal{L}(\dot{d}, \dot{q}, d, q) = \left\{ \frac{1}{2} q^{2/3} \dot{d} \cdot [M\dot{d}] - V(q^{1/3} d) + \frac{\mu}{2} \dot{q}^2 - \alpha q \right\}. \quad (52)$$

We interpret q as the (dynamic) value of the volume $V$ and call this additional degree of freedom the 'piston' degree of freedom. The constant $\alpha$ corresponds to the external pressure acting on the system and $\mu > 0$ is the mass of the 'piston'.

Upon defining $\mathbf{q} = (d^T, q)^T \in \mathbb{R}^{m\bar{m}}$, $\bar{m} = 3N+1$, we find that (52) fits into the general form (2) with non-constant mass matrix $$\mathcal{M}(\mathbf{q}) = \begin{bmatrix} q^{2/3} M & 0 \\ 0 & \mu \end{bmatrix}. \quad (53)$$

The associated NPE equations of motion are now easily derived using (3). See also Andersen's original publication [16]. The conserved energy $\mathcal{H}$ can be derived from the Lagrangian density (52) according to the standard formula (5), i.e., $$\mathcal{H} = \dot{d} \cdot \nabla_{\dot{d}} \mathcal{L} + \dot{q} \nabla_{\dot{q}} \mathcal{L} - \mathcal{L} \quad (54)$$

$$= \frac{1}{2} q^{2/3} \dot{d} \cdot [M\dot{d}] + \frac{\mu}{2} \dot{q}^2 + V(q^{1/3} d) + \alpha q$$

$$= \frac{1}{2} q^{-2/3} p_d \cdot [M^{-1} p_d] + \frac{1}{2\mu} p^2 + V(q^{1/3} d) + \alpha q$$

$$= \frac{1}{2} p_r \cdot [M^{-1} p_r] + V(r) + \frac{1}{2\mu} p^2 + \alpha q,$$

where $$p_d = q^{2/3} M \dot{d}, \quad p = \mu \dot{q} \quad (55)$$

are the conjugate momenta in the NPE formulation and $p_r = M\dot{r} = p_d/q^{1/3}$ is the classical momentum vector of the NVE formulation (44).

2. A Time-Reversible and Symplectic Implementation

We use the previously developed discrete variational principle to derive a symplectic time-stepping method and obtain the generalized leapfrog method $$\delta_t^+ \left\{ \frac{1}{2} [(q^n)^{2/3} + (q^{n-1})^{2/3}] M \delta_t^- d^n \right\} = -\nabla_d V((q^n)^{1/3} d^n) \quad (56)$$

and $$\mu \delta_t^+ \delta_t^- q^n = \quad (57)$$
$$\frac{(q^n)^{-1/3}}{6} \{ \delta_t^+ d^n \cdot [M \delta_t^+ d^n] + \delta_t^- d^n \cdot [M \delta_t^- d^n] \} - \alpha - \nabla_q V((q^n)^{1/3} d^n).$$

The equivalent generalized Störmer-Verlet formulation is defined as follows. Given $(d^n, q^n, p_d^n, p^n)$, we first find $d^{n+1}$ and $q^{n+1}$ from the equations $$p_d^n = \frac{1}{2}[(q^{n+1})^{2/3} + (q^n)^{2/3}] M \left( \frac{d^{n+1} - d^n}{\Delta t} \right) + \frac{\Delta t}{2} \nabla_d V((q^{1/3})^n d^n) \quad (58)$$

and $$p^n = \mu \left( \frac{q^{n+1} - q^n}{\Delta t} \right) - \frac{\Delta t}{6} (q^n)^{-1/3} \left( \frac{d^{n+1} - d^n}{\Delta t} \right) \cdot \left[ M \left( \frac{d^{n+1} - d^n}{\Delta t} \right) \right] + \quad (59)$$
$$\frac{\Delta t}{2} [\nabla_q V((q^n)^{1/3} d^n) + \alpha].$$

The values for $p_d^{n+1}$ and $p^{n+1}$ are explicitly given by $$p_d^{n+1} = \frac{1}{2}[(q^{n+1})^{2/3} + (q^n)^{2/3}] M \left( \frac{d^{n+1} - d^n}{\Delta t} \right) - \frac{\Delta t}{2} \nabla_d V((q^{n+1})^{1/3} d^{n+1}) \quad (60)$$

and $$p^{n+1} = \mu \left( \frac{q^{n+1} - q^n}{\Delta t} \right) + \frac{\Delta t}{6} (q^{n+1})^{-1/3} \left( \frac{d^{n+1} - d^n}{\Delta t} \right) \cdot \left[ M \left( \frac{d^{n+1} - d^n}{\Delta t} \right) \right] - \quad (61)$$
$$\frac{\Delta t}{2} [\nabla_q V((q^{n+1})^{1/3} d^{n+1}) + \alpha].$$

This completes one time step.

The time-reversible and symplectic method (58)-(61) allows for the implementation of a hybrid Monte Carlo methods as proposed in [2] and described in more detail in [23]. We now derive a fourth-order modified energy for the GSHMC method.

Let Q(t) and D(t) denote the interpolation polynomials along numerical trajectories $\{q^n\}$ and $\{d^n\}$, respectively. Then the associated fourth-order modified energy, defined by (33), is given by $$\mathcal{H}_{\Delta t}^{[4]} = \mathcal{H} + \frac{\Delta t^2}{24} [2\mu \dot{Q} Q^{(3)} - \mu \ddot{Q}^2] + \frac{\Delta t^2}{24} \{4\dot{D} \cdot [Q^{2/3} M D^{(3)}] - \quad (62)$$
$$6\dot{D} \frac{d}{dt} [Q^{2/3} M \ddot{D}] + 4\dot{D} \cdot \frac{d^2}{dt^2} [Q^{2/3} M \dot{D}] \} + \frac{\Delta t^2}{24} \{3\ddot{D} \cdot$$
$$[Q^{2/3} M \ddot{D}] - 4\ddot{D} \cdot \frac{d}{dt} [Q^{2/3} M \dot{D}] \}$$
$$= \mathcal{H} + \frac{\Delta t^2}{24} \{2\mu \dot{Q} Q^{(3)} - \mu \ddot{Q}^2 + 2 Q^{2/3} \dot{D} \cdot [M D^{(3)}] - Q^{2/3} \ddot{D} \cdot$$
$$[M \ddot{D}] \} + \frac{\Delta t^2}{12} \left\{ \left( \frac{4\ddot{Q}}{3Q^{1/3}} - \frac{4\dot{Q}^2}{9Q^{4/3}} \right) \dot{D} \cdot [M\dot{D}] - \frac{2}{3Q^{1/3}} \dot{Q} \dot{D} \cdot$$
$$[M\ddot{D}] \}$$

with $\mathcal{H}$ given by (54).

3. A Modified PMMC Step

The one-step formulation (58)-(59) together with (60)-(61) will be used in the GSHMC method according to preferred invention embodiments. After each completed NPE molecular dynamics sub-step, we refresh the momenta $p_d$ and $p$ as described in Section IV.

Following the Langevin piston method of Feller et al. [17], one can also apply the following simplified momentum update. We always keep the particle momentum $p_d$ d and only refresh the "piston" momentum $p$, i.e., we replace (11) by $$u'_d = d, \quad (63)$$

$$p'_d = -p_d, \quad (64)$$

$$u' = \sin(\phi)p + \cos(\phi)u \quad (65)$$

$$\overline{p} = -\cos(\phi)\overline{p} + \cos(\phi)u, \quad (66)$$

with $$u = \beta^{-1}\mu^{1/2}\xi, \ \xi \sim N(0,1). \quad (67)$$

The probability (37) is replaced by $$P(d, q, p_d, p, u, p', u') = \quad (68)$$

$$\min\left(1, \frac{\exp\left(-\beta\left[\mathcal{H}_{\Delta t}(d, q, p_d, p') + \frac{1}{2\mu}(u')^2\right]\right)}{\exp\left(-\beta\left[\mathcal{H}_{\Delta t}(d, q, p_d, p) + \frac{1}{2\mu}\mu^2\right]\right)}\right),$$

where $\mathcal{H}_{\Delta t}$ is an appropriate modified energy, e.g., $\mathcal{H}_{\Delta t} = \mathcal{H}_{\Delta t}^{[4]}$ with $\mathcal{H}_{\Delta t}^{[4]}$ given by (62).

Given a collision frequency $\gamma$ for the Langevin piston method [17], we choose $\phi$ and $\tau = L\Delta t$ such that $\phi = \sqrt{2\gamma\tau} \ll 1$ and the resulting GSHMC method can be viewed as a rigorous implementation of the Langevin piston method in the sense of section IIC under the assumption of ergodicity of the induced Markov process. Note that, on the contrary, the Langevin piston method combined with the Brunger, Brooks, Karplus (BBK) time-stepping algorithm [24] leads to statistical errors proportional to $\Delta t^2$. In particular, one needs to require that $\gamma\Delta t$ is small.

VI. ALGORITHMIC SUMMARY OF THE GSHMC METHOD

We summarize the algorithmic implementation of an embodiment of the GSHMC method for the fourth-order modified energy (33) as follows:

A. MDMC Step of GSHMC

Given an accepted MC sample with generalized position vector q and momentum vector p, we determine the associated modified energy $\mathcal{H}_{\Delta t}^{[4]}(q,p)$ by integrating the equations of motion two steps forward and backward in time using (22)-(23) in order to construct the required interpolation polynomial Q(t) as defined in section IV A.

The equations of motion are then solved forward in time over L time steps using the symplectic and time-reversible method (22)-(23). Denote the result by (q',p').

An additional two time steps are performed to evaluate the associated modified energy $\mathcal{H}_{\Delta t}^{[4]}(q',p')$ and the proposal step (q',p') is accepted with probability $$\min(1, \exp(-\beta\{\mathcal{H}_{\Delta t}^{[4]}(q',p') - \mathcal{H}_{\Delta t}^{[4]}(q,p)\})). \quad (69)$$

In case of rejection, we continue with (q',p')=(q,-p).

B. PMMC Step of GSHMC

Using a change of variables as, for example, defined by (41), we first compute $\overline{p}' = \psi(q',p',\Delta t)$. The momentum vector $\overline{p}'$ is now mixed with a noise vector u distributed according to (12). We formally set q"=q' and define $$\begin{pmatrix} u' \\ \overline{p}'' \end{pmatrix} = \begin{pmatrix} \cos(\phi) & -\sin(\phi) \\ \sin(\phi) & \cos(\phi) \end{pmatrix} \begin{pmatrix} u \\ \overline{p}' \end{pmatrix}. \quad (70)$$

The proposal momentum vector p", implicitly defined by $\overline{p}'' = \psi(q'',p'',\Delta t)$, is accepted with probability $$\min\left(1, \frac{\exp\left(-\beta\left[\mathcal{H}_{\Delta t}^{[4]}(q'', p'') + \frac{1}{2}(u')^T \mathcal{M}(q'')^{-1} u'\right]\right)}{\exp\left(-\beta\left[\mathcal{H}_{\Delta t}^{[4]}(q', p') + \frac{1}{2}u^T \mathcal{M}(q')^{-1} u\right]\right)}\right), \quad (71)$$

where two time steps forward and backwards need to be performed in order to evaluate $\mathcal{H}_{\Delta t}(q'',p'')$. In case of rejection, we continue with (q",p")=(q',p').

A single GSHMC step is now completed. We store the accepted MC sample as $(q_{i+1},p_{i+1})=(q'',p'')$ and evaluate the associated weight factor $w_{i+1}$ using (43).

C. Comments

We summarize here a few general comments on the GSHMC method according to preferred invention embodiments.

(i) Note that different angles $\phi$ can be assigned to different components of u and $\overline{p}'$ in (70). This freedom has been used in section V B 3.

(ii) Note also that the summary of the GSHMC method has been formulated such that the number of necessary momentum flips is minimized. This is in contrast to the (entirely equivalent) presentation used so far, which has been based on the detailed balance requirement.

(iii) The number of additional force evaluations for GSHMC with $\overline{p}=p$ over standard HMC amounts to p−2, where p is the order of the modified energy. For example, GSHMC with (33) requires two additional force evaluations per complete Monte Carlo step.

The change of variables (41) requires additional force evaluations [12].

(iv) The time step $\Delta t$ and the angle $\phi$ should be chosen such that the probability of having both the MDMC as well as the PMMC step being simultaneously rejected is less than 1%. This is because we obtain $q_{i+1}=q_i$ and $p_{i+1}=-p_i$ in such a case, which leads to the undesired Zitterbewegung in the MC samples.

This requires, in general, a decrease of $\phi$ in (70) as the system size, d=3N, increases. Furthermore, the discussion in [16] on a dynamically consistent collision frequency $\gamma$ for a small volume of liquid surrounded by a much larger volume suggests that $\phi \propto \gamma^{1/2} \propto 1/N^{1/3}$, where N is the number of atoms.

(v) In case the PMMC step is performed with a change of variables as defined, for example, by (41) to replace p with a linear constitution of atoms, we refer to the resulting method as the GS2HMC method (in analogy to the S2HMC method of [12]).

In case of $\overline{p}=p$, we continue using the acronym GSHMC.

VII. NUMERICAL RESULTS

Preferred embodiments of the present invention will now be described, purely by way of example, with reference to the accompanying drawings, in which.

Figure 1:
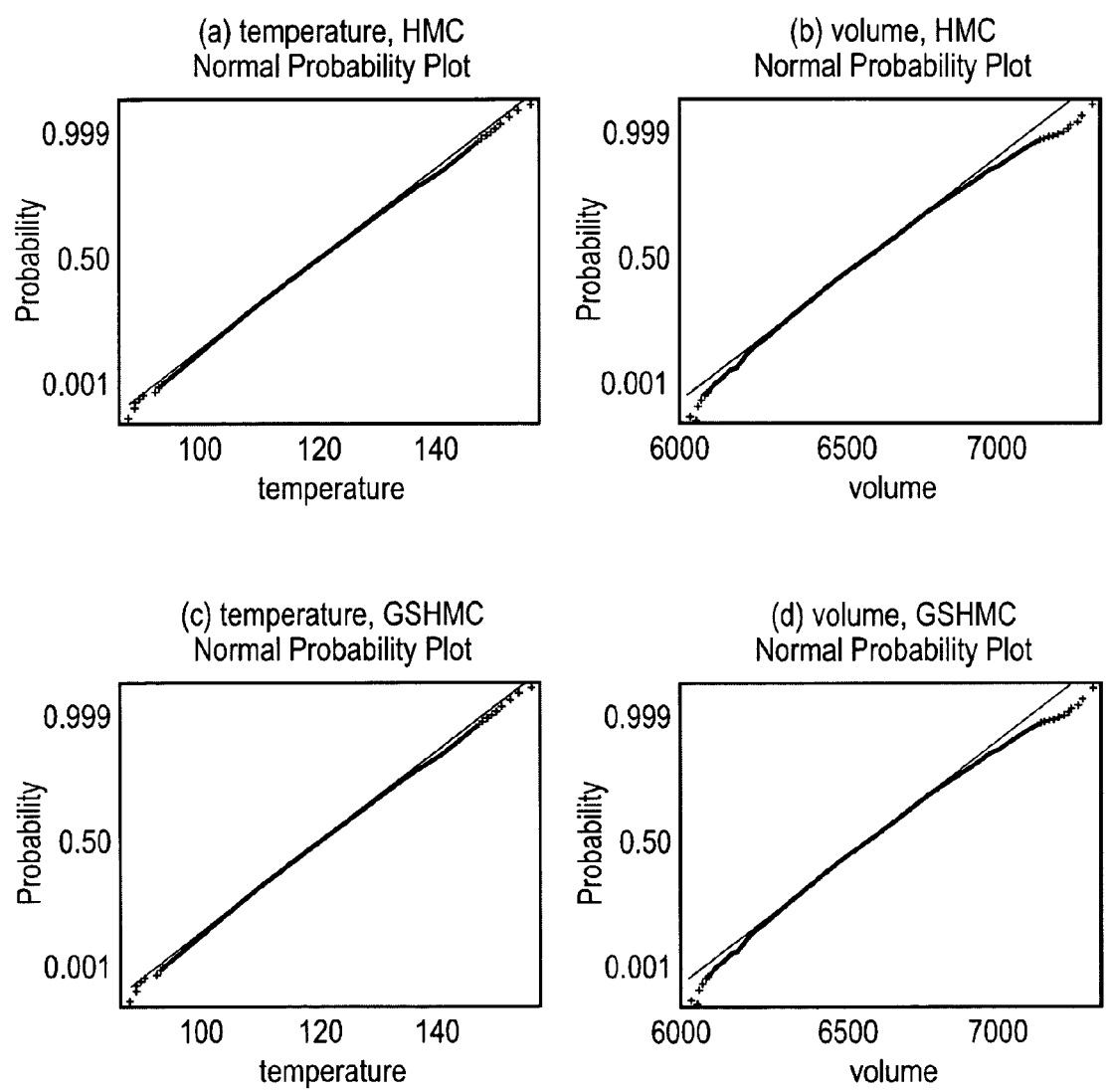
FIG. 1 shows normal probability plots for volume and temperature fluctuations from HMC and GSHMC implementation of Andersen's constant pressure formulation.

In this section, we perform three sets of experiments forming three demonstrations of embodiments of the invention. The first set is based on an NVT simulation of argon and assesses rejection rates for several MC methods in the context of sampling. The second set of experiments is based on an NPT simulation of argon. Here we compare the GSHMC algorithm and the Langevin piston method of Feller et al. [17] and assess the performance of GSHMC in the context of stochastic dynamics simulations. We finally implement GSHMC for a larger biomolecular system, the bacteriophage T4 lysozyme protein, and compare the sampling efficiency of GSHMC to constant temperature MD using the Berendsen thermostat [25].

Argon

We perform simulations for argon in a periodic box under an NVT and NPT, respectively, ensemble. We now present numerical results for both ensembles. We begin with the NVT simulations.

1. NVT Simulations

We perform NVT simulations at a temperature of T=120 K using the following two settings:

(A) $N=5^3$, $L=20.1$ Å,
(B) $N=8^3$, $L=319.6$ Å.

We implement the GSHMC method with three values of the angle $\phi$ ($\pi/2$, $\phi=\pi/4$ and $\phi=\pi/8$) in the PMMC step. We also implement the GSHMC method with the modified momentum refreshment step, as defined by (41), with $\phi=\pi/2$. We refer to this implementation as GS2HMC.

Results are compared to implementations of the standard HMC method and the newly proposed S2HMC method of [12].

All Monte Carlo (MC) implementations use $\tau=L\Delta t=2.17$ ps and generate a total of $K=10^4$ Monte Carlo samples to compute expectation values according to (42). Simulations are performed for four different values of $\Delta t$ ($\tau/50 \approx 43.4$ fs, $\tau/75 \approx 28.9$ fs, $\tau/100 \approx 21.7$ fs, $\tau/200 \approx 10.9$ fs).

TABLE I

Rejection rates for MDMC and PMMC steps, respectively, for all tested methods under the experimental setting A.

| MDMC/PMMC rejections | $\Delta t \approx$ 43.4 fs | $\Delta t \approx$ 28.9 fs | $\Delta t \approx$ 21.7 fs | $\Delta t \approx$ 10.9 fs |
|---|---|---|---|---|
| GSHMC method, $\phi = \pi/2$ | 20%/23% | 2%/12% | <1%/6% | <1%/2% |
| GSHMC method, $\phi = \pi/4$ | 22%/17% | 2%/8% | <1%/4% | <1%/1% |
| GSHMC method, $\phi = \pi/8$ | 21%/9% | 2%/5% | <1%/2% | <1%/<1% |
| GS2HMC method, $\phi = \pi/2$ | 19%/<1% | 2%/<1% | <1%/<1% | <1%/<1% |
| S2HMC method | 20%/NA | 1%/NA | <1%/NA | <1%/NA |
| HMC method | 22%/NA | 9%/NA | 6%/NA | 2%/NA |

TABLE II

Rejection rates for MDMC and PMMC steps, respectively, for all tested methods under the experimental setting B.

| MDMC/PMMC rejections | $\Delta t \approx$ 43.4 fs | $\Delta t \approx$ 28.9 fs | $\Delta t \approx$ 21.7 fs | $\Delta t \approx$ 10.9 fs |
|---|---|---|---|---|
| GSHMC method, $\phi = \pi/2$ | 33%/37% | 3%/19% | <1%/10% | <1%/3% |
| GSHMC method, $\phi = \pi/4$ | 33%/27% | 3%/12% | <1%/7% | <1%/3% |
| GSHMC method, $\phi = \pi/8$ | 32%/15% | 3%/7% | <1%/4% | <1%/1% |
| GS2HMC method, $\phi = \pi/2$ | 32%/<1% | 3%/<1% | <1%/<1% | <1%/<1% |
| S2HMC method | 33%/NA | 2%/NA | <1%/NA | <1%/NA |
| HMC method | 99%/NA | 15%/NA | 10%/NA | 3%/NA |

We state rejection rates for the MDMC step and the PMMC step (where applicable) in table I for setting A and in table II for setting B, respectively. We observe an increase in rejection rates for all methods for increasing system size d and step-size $\Delta t$. The acceptance rate for the MDMC step is similar for all GSHMC and S2HMC implementations and is consistently better than the corresponding rate of standard HMC. The acceptance rate of PMMC step in GSHMC improves with smaller values of $\phi$. The GS2HMC method almost reaches the perfect behaviour of S2HMC and HMC in terms of momentum resampling. One should note, however, that the transformation step (41) requires additional force evaluations.

TABLE III

Expectation values and their standard deviation range for total energy, E, diffusion constant, D, and pressure, P, from numerical experiments using setting A and $\Delta t \approx 28.9$ fs.

| | energy E [120 $k_b$ K] | diffusion D [Å$^2$ ps$^{-1}$] | pressure P [kN/cm$^2$] |
|---|---|---|---|
| GSHMC method, $\phi = \pi/2$ | −442.6 ± 33.6 | 0.2873 ± 0.0564 | 0.5904 ± 0.7302 |
| GSHMC method, $\phi = \pi/4$ | −442.7 ± 32.8 | 0.4782 ± 0.1275 | 0.5881 ± 0.7204 |
| GSHMC method, $\phi = \pi/8$ | −442.0 ± 31.2 | 0.7742 ± 0.1465 | 0.5958 ± 0.7049 |
| GS2HMC method, $\phi = \pi/2$ | −441.0 ± 33.2 | 0.2927 ± 0.0205 | 0.6515 ± 0.7317 |
| S2HMC method | −441.9 ± 32.6 | 0.2877 ± 0.0668 | 0.6630 ± 0.7266 |
| HMC method | −438.0 ± 33.8 | 0.2691 ± 0.0219 | 0.6571 ± 0.7344 |

We also give expectation values of total energy, E, diffusion constant, $$D = \frac{1}{6Nt}\|r(t) - r(0)\|^2,  \quad (72)$$

and pressure, P, as well as their standard deviation range (corresponding to the 95% confidence interval of normally distributed data) for the experimental setting A and $\Delta t=\tau/75\approx 28.9$ fs in table III. All methods lead to comparable results in terms of total energy, E, implying that all methods correctly sample from the canonical ensemble. More remarkably, the diffusion constant, D, increases significantly for smaller values of $\phi$ in the PMMC step of GSHMC. This confirms the fact that HMC methods influence the dynamical properties of a molecular system. Pressure, P, fluctuates largely for all methods, which is not unexpected for a small molecular system such as that of setting A.

2. NPT Simulations

We now simulate N=125 argon atoms at constant temperature T=120 K and constant pressure P=0.65·10$^7$ N m$^{-2}$.

We implement a standard constant pressure and temperature HMC algorithm (see, e.g., [23]) and compare the results to the corresponding GSHMC implementation of section VB with $\phi=\pi/2$.

The simulation parameters are as follows. Both methods are implemented with a step-size of $\Delta t=10.9$ fs, samples are taken at in intervals of $\tau=L\Delta t=2.17$ ps, i.e., L=200, and the total number of samples is K=10$^4$. The mass of the piston degree of freedom is set equal to $\mu=6$, and $\alpha=0.65\cdot 10^7$ N m$^{-2}$.

Feller et al [17]. The Langevin piston equations of motion are implemented using the Brunger, Brooks, Karplus (BBK) algorithm [24].

The simulation parameters are now as follows. Both methods are implemented with a step-size of $\Delta t=21.7$ fs, samples are taken at in intervals of $\tau=L\Delta t=0.217$ ps, i.e., L=10, and the total number of samples is K=2×10$^4$. The mass of the piston degree of freedom is set equal to $\mu=6$, $\alpha=0.65\cdot 10^7$ N m$^{-2}$, and the collision frequency in the Langevin piston is set equal to $\gamma=0.1152$ ps$^{-1}$. The angle, $\phi$, in (65)-(66) is determined according to $\phi=\sqrt{2\Delta t\gamma}\approx 0.2236$. Both methods are started from an equilibrated configuration.

We compare pressure, P, temperature, T, and total energy, E. Mean values and their standard deviation range can be found in table V. Note that both methods couple to a constant temperature 'heat bath' only through the piston degree of freedom. The results from both methods are in agreement (to within the expected errors given the simulation length, the system size, and the weak coupling to the 'heat bath') with the desired NPT ensemble.

B. Lysozyme Protein in Water

A larger molecular system, the bacteriophage T4 lysozyme protein (pdb entry 2LZM), is simulated to compare the sampling efficiency of GSHMC and constant temperature MD. A united atoms representation is used to eliminate all hydrogen atoms from the protein, and water is modelled using the SPC model [26]. The total number of atoms is 23207, which are placed in a rhombic dodecahedron simulation box. Both simulation approaches, MD and GSHMC, use GROMACS

TABLE IV

Mean values and their standard deviation range for pressure, P, temperature, T, and total energy, E, for GSHMC and HMC implementation of Andersen's constant pressure formulation.

| | pressure [× 10$^7$ N m$^{-2}$] | temperature [K] | energy [120 k$_B$ K] |
|---|---|---|---|
| GSHMC method $\phi = \pi/2$ | 0.6492 ± 0.8450 | 120 ± 17 | −330 ± 49 |
| HMC method | 0.6342 ± 0.8404 | 120 ± 17 | −331 ± 49 |

TABLE V

Mean values and their standard deviation range for pressure, P, temperature, T, and total energy, E, for GSHMC and Langevin piston BBK simulation of the NPT ensemble.

| | pressure [×10$^7$ N m$^{-2}$] | temperature [K] | energy [120 k$_B$ K] |
|---|---|---|---|
| GSHMC method | 0.6500 ± 0.8425 | 118 ± 14 | −340 ± 11 |
| Langevin piston, BBK algorithm | 0.6477 ± 0.8580 | 123 ± 18 | −314 ± 45 |

We compare pressure, P, temperature, T, and total energy, E. Mean values and their standard deviation range can be found in table IV. We also verify that the volume and temperature fluctuations are Gaussian distributed. We display the results for the GSHMC and HMC method in FIG. 1. Both methods lead to very similar distributions. The temperature distribution is almost ideal while the volume fluctuations display some non-Gaussian behaviour in the tails. The effect can be attributed to the finite size of the sample.

We also implement the constant pressure and temperature GSHMC algorithm using the partial momentum update (63)-(66) and compare the results to the Langevin piston method of 3.2.1 [27] to perform the molecular dynamics steps. Specifically, a switch cut-off scheme is used for Lennard-Jones interactions. Coulomb interactions are treated using a particle-mesh Ewald summation (PME) method [28, 29]. The full direct and reciprocal space parts are calculated in each step and a lattice spacing of 0.1 nm is applied. All bonds are constrained using the SHAKE method [22] with a relative tolerance of 10$^{-12}$ allowing for a step-size of $\Delta t=2$ fs.

The system is initially equilibrated for 1 ns using standard MD techniques. The MD and GSHMC simulations are then performed for another 1 ns at a temperature of 300 K. In the traditional MD approach the temperature is coupled to a heat bath of 300 K using the Berendsen thermostat with a coupling time constant of 0.1 ps [25].

To find the optimal settings for GSHMC production stage we investigate the effect of different simulation parameters on the sampling efficiency of GSHMC. A set of comparatively short simulations are performed using three different step-sizes $\Delta t$ (1, 2 and 4 fs), two different MD simulation lengths $\tau$ (2 and 4 ps), five values of the angle $\phi$ ($\pi/24$, $\pi/12$, 0.3 0.5, $\pi/2$) and two values of the order p (4, 6) for the modified Hamiltonian $\mathcal{H}^{[p]}$. The results of this study are shown in FIGS. 2 and 3.

Since we found that acceptance rate for MDMC step was consistently high (98-100%) for all tested parameters, we present here the results for the acceptance rate in the PMMC step only. FIG. 2 demonstrates the effect of step-size and MD simulation length on the momentum acceptance rates whereas FIG. 3 shows how the momentum acceptance rate depends on the angle $\phi$. The momentum acceptance rate was found to be essentially independent of the order (here 4th and 6th order) of the modified energies.

Figure 2:
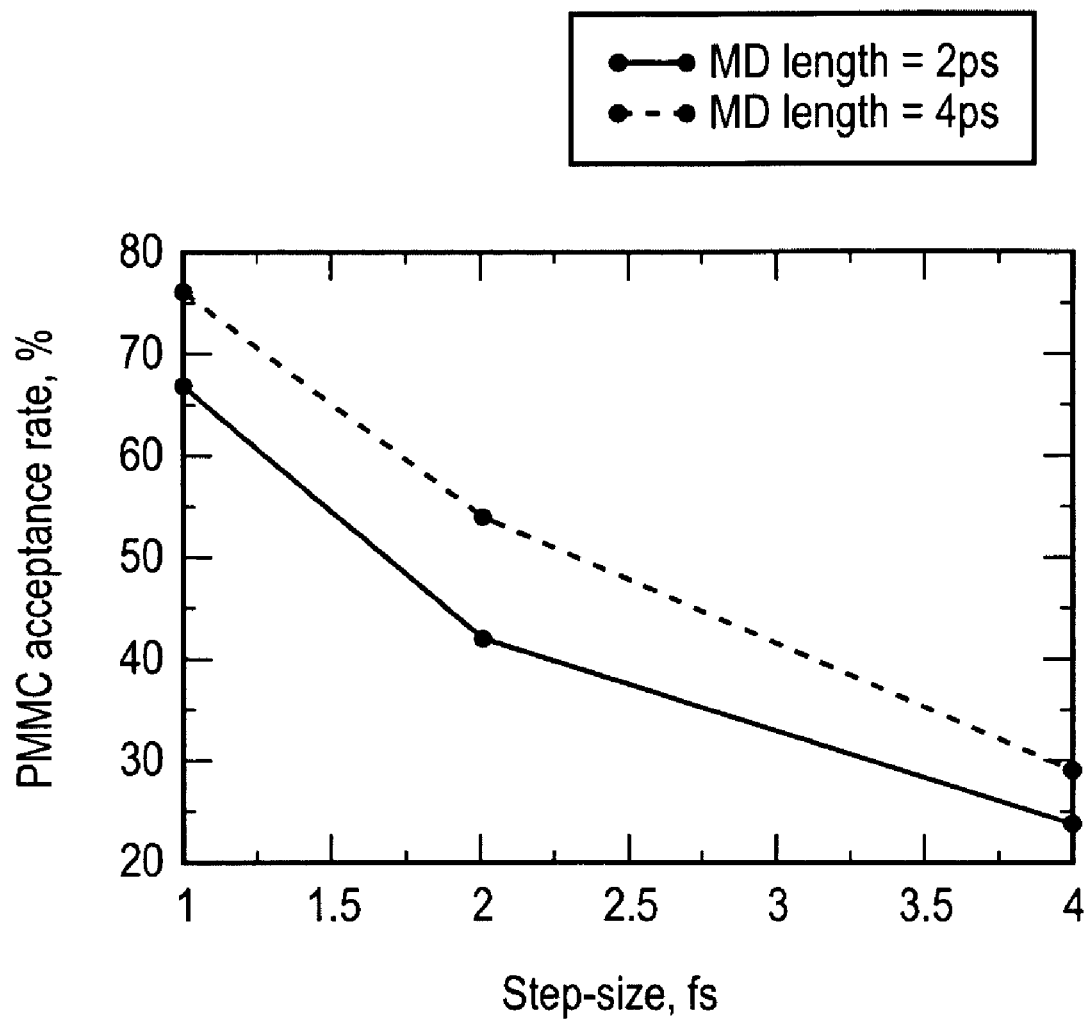
FIG. 2 shows PMMC acceptance rate vs. MD step-size $\Delta t$ and MD length $\tau$ for fixed angle $\phi=\pi/24$.
Figure 3:
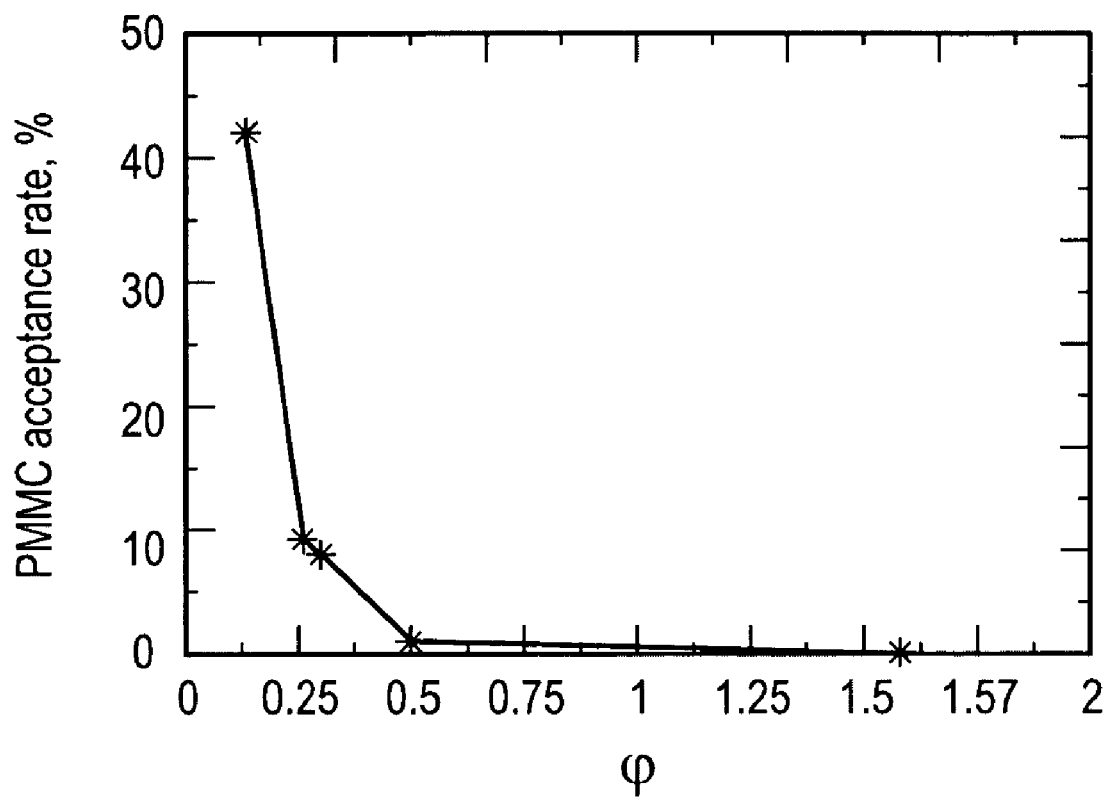
FIG. 3 shows PMMC acceptance rate vs. $\phi$ for fixed step-size $\Delta t=2$ fs and MD simulation length $\tau=2$ ps.

It can be concluded from FIGS. 2 and 3 that smaller step-sizes, larger MD simulation lengths, and smaller values of $\phi$ induce a higher acceptance rate in the PMMC step. A nearly optimal choice of the parameter $\phi$ and the step-size $\Delta t$ is crucial for the performance of GSHMC. Choosing $\phi = \pi/2$ is found to be not efficient for this large system.

We have to stress that the PMMC step is cheap compared with the MDMC step. To decrease the rejection rate of the PMMC step one can repeat the step a desired number of times. This strategy is efficiently implemented in parallel in our code.

Figure 4:
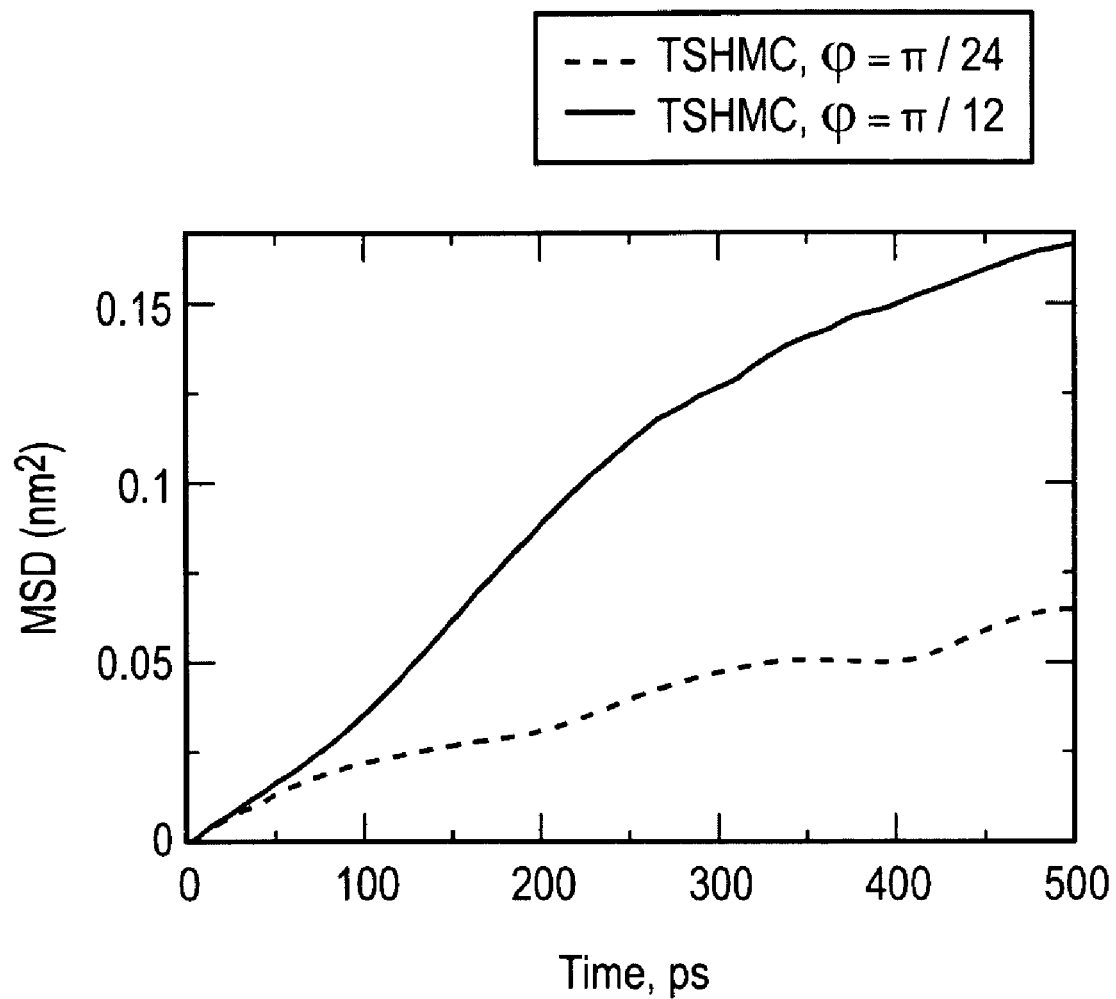
FIG. 4 shows mean-square displacements of the protein centre-of-mass vs. $\phi$.

In addition, we consider the evolution of the mean-square displacement of the centre-of-mass (c.o.m.) of the protein for GSHMC simulations using two different values of $\phi = \pi/24$ and $\phi = \pi/12$. We find that the c.o.m. mobility of the protein in GSHMC simulation increases with an increasing of $\phi$. This is shown in FIG. 4.

To perform a comparison between GSHMC and MD simulations we run the GSHMC simulation with a step-size of $\Delta t = 2$ fs, the number of MD steps in MDMC equal to L=1000, and $\phi = \pi/12$ on ten processors of a PC cluster. We use a sixth-order modified energy.

To compare the sampling efficiency of different sampling methods with respect to an observable $\Omega$, we evaluate the integrated autocorrelation function values of a time series $\{\Omega_i\}_{i=1}^K$, where K is the number of samples [15]. The integrated autocorrelation function value is defined by $$A_\Omega = \sum_{l=1}^{K'} C(\tau_l), \qquad (73)$$

where $C(\tau_l)$, L=1 ..., K is the standard autocorrelation function for the time series $\{\Omega_i\}_{i=1}^K$ with the normalization $C(\tau_0) = C(0) = 1$. The integrated autocorrelation function value provides a good measure for the efficiency of a sampling method since, on average, $1 + 2A_\Omega$ correlated measurements $\Omega_i$ are needed to reduce the variance by the same amount as a single truly independent measurement of $\Omega$.

Figure 5:
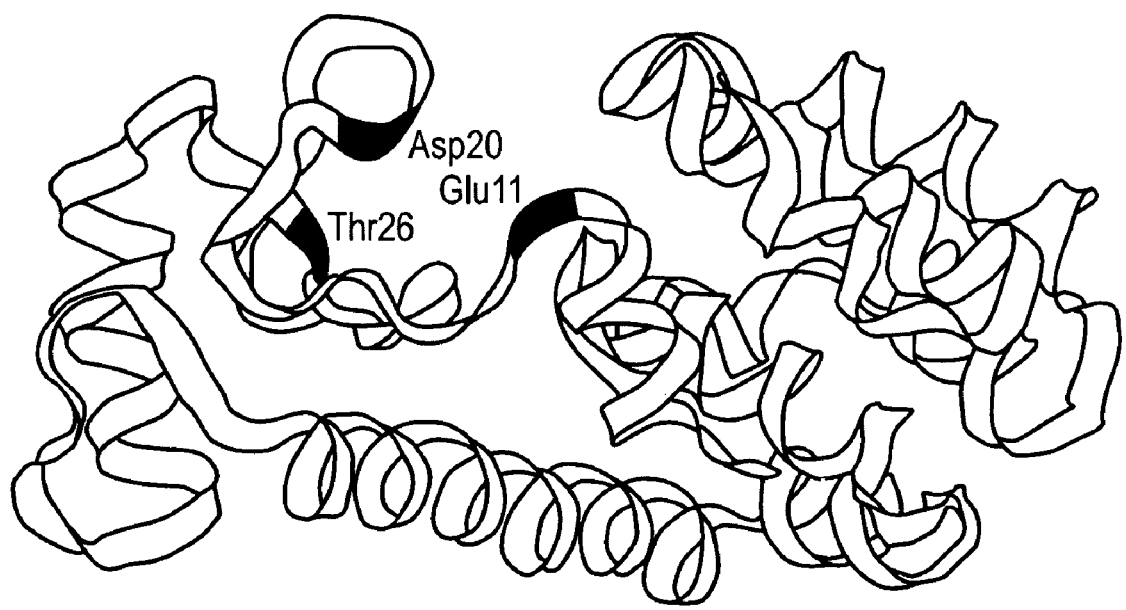
FIG. 5 shows VMD [29] ribbon diagram of 2LZM illustrating locations of catalytic residues Glu11, Asp20, and Thr26.

We present the autocorrelation functions for the dihedrals of Asp20, Glu11 and Thr26 residues in FIG. 5. These dihedrals are known to be critical catalytic residues in lysozyme. In fact, it has been reported that the catalytic activity of most lysozymes is largely due to three amino acids. In the case of the bacteriophage T4 lysozyme, catalysis takes place due to the concerted action of Glu11, Asp20, and Thr26 with the substrate [31-35].

Figure 6:
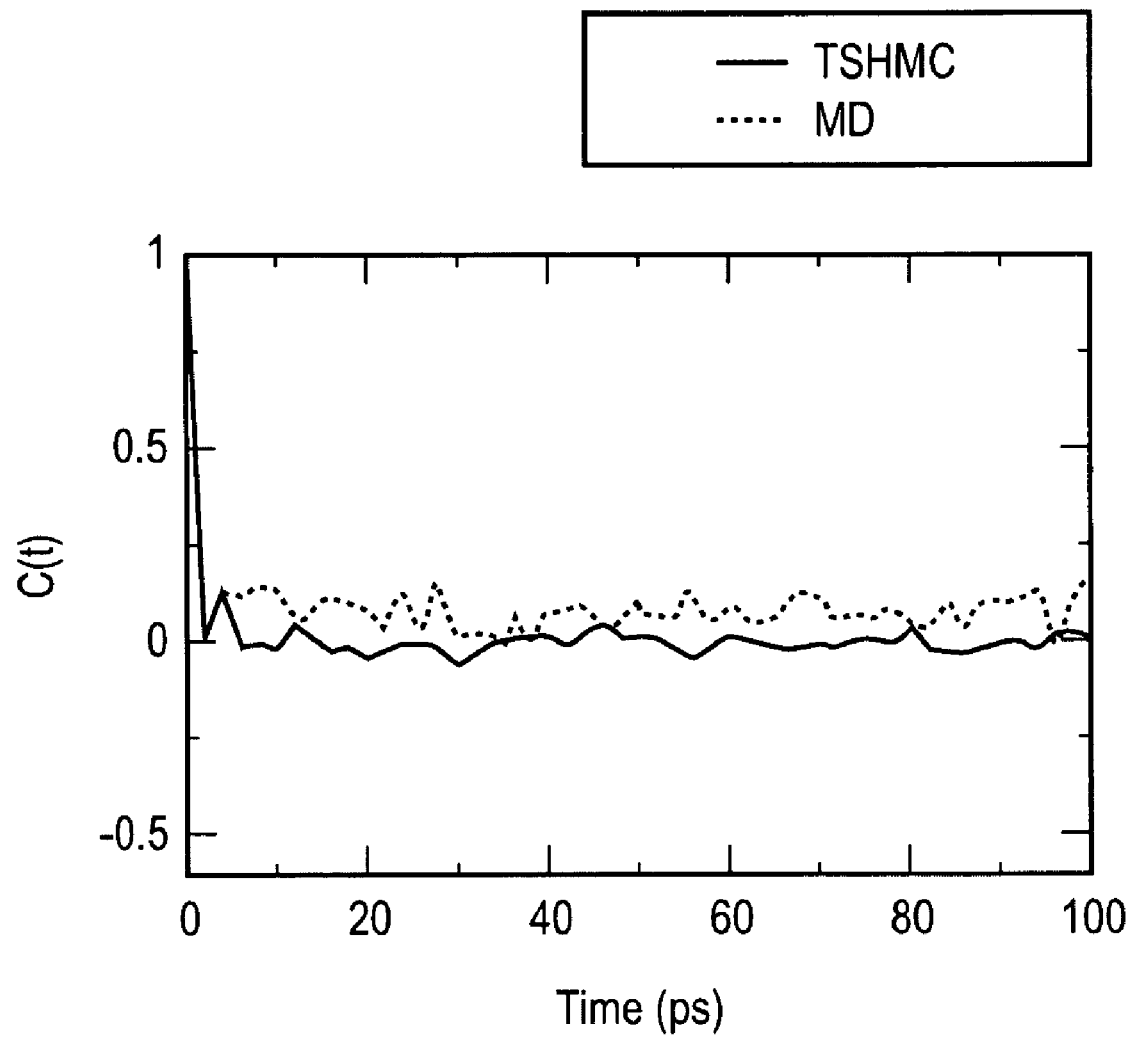
FIG. 6 shows autocorrelation function of main chain torsion angle $\Phi$ of residue Thr26.
Figure 7:
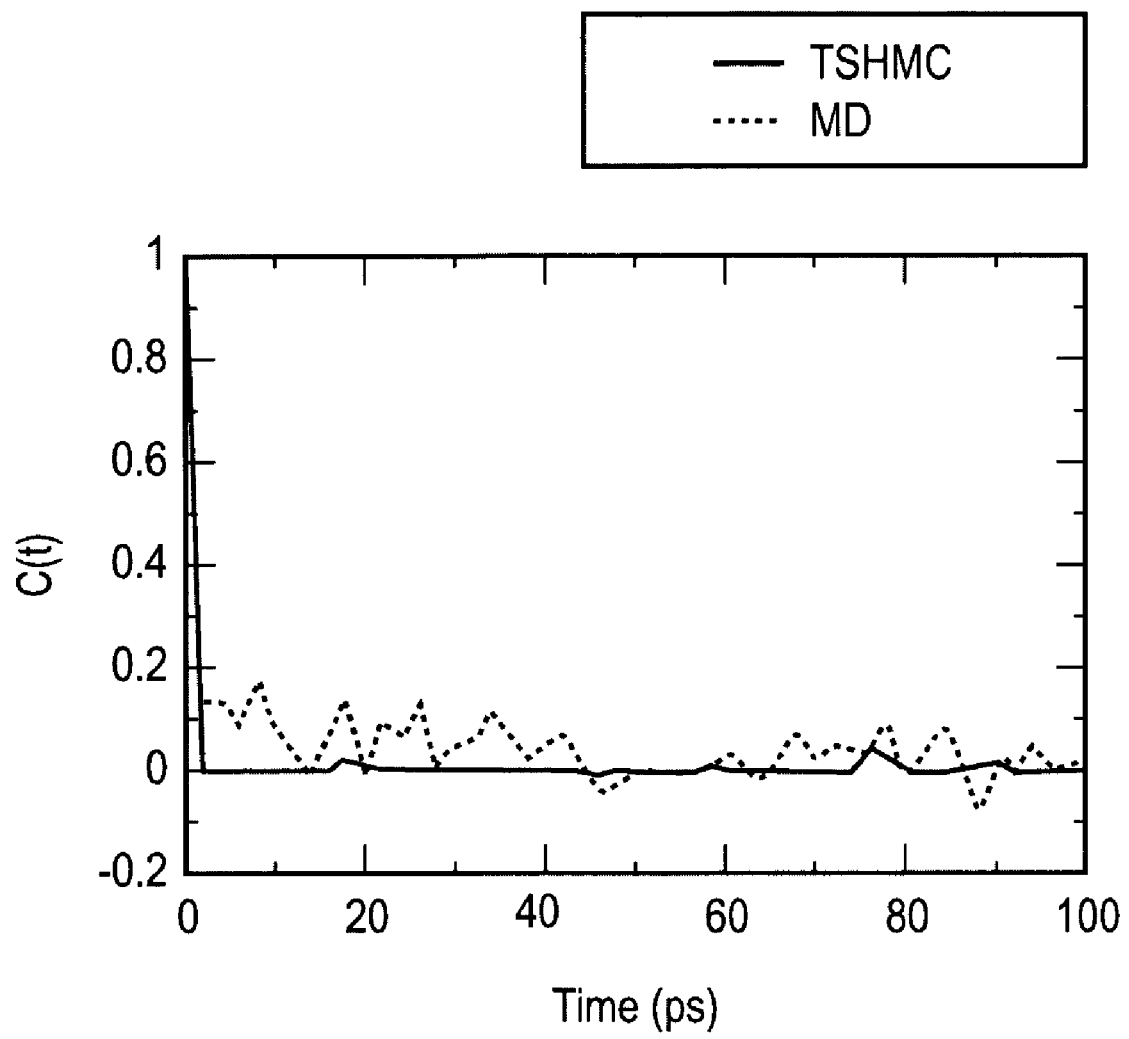
FIG. 7 shows autocorrelation function of main chain torsion angle $\Psi$ of residue Thr26.
Figure 8:
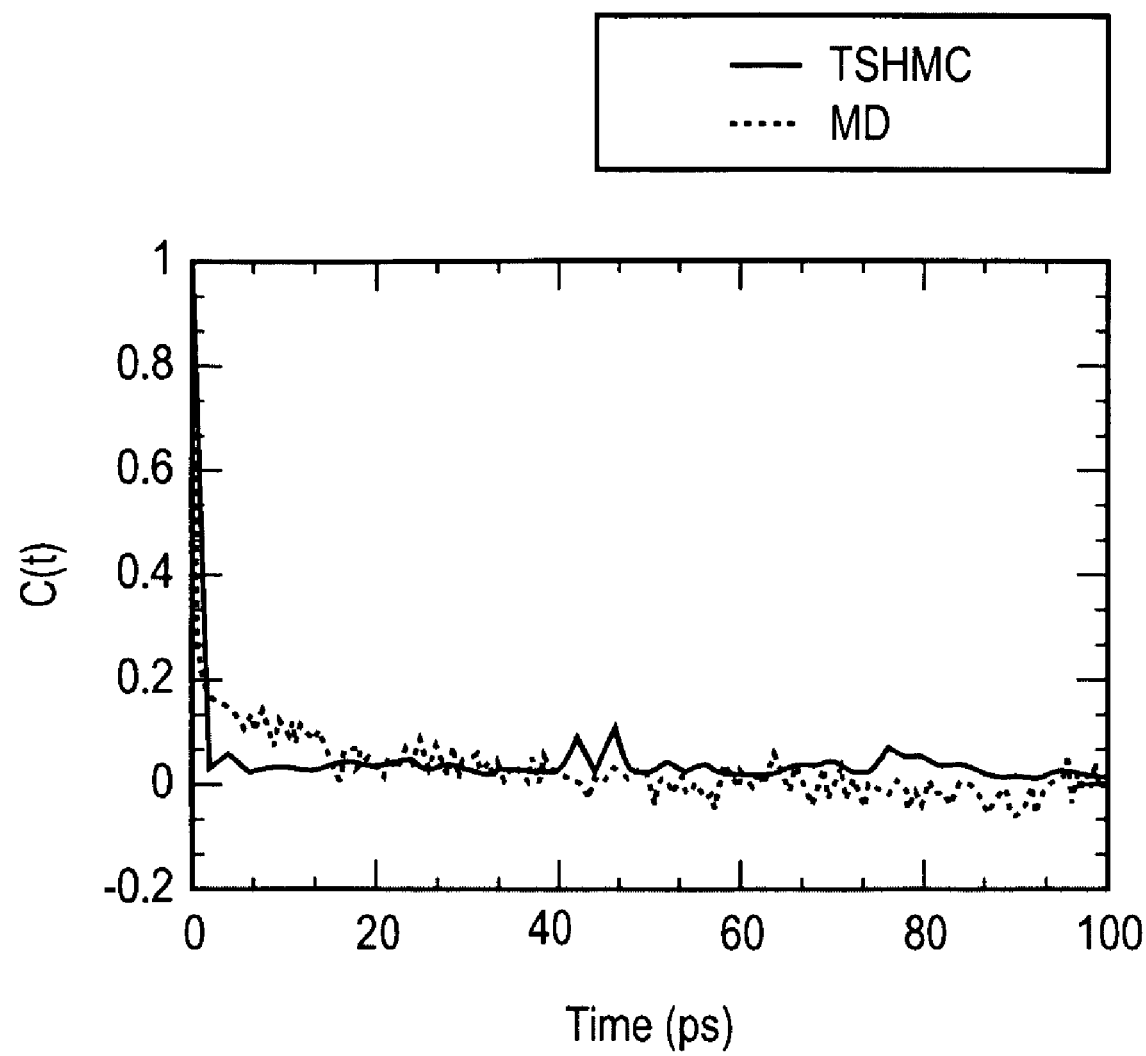
FIG. 8 shows autocorrelation function of side chain torsion angle $X_1$ of residue Thr26.

The autocorrelation functions $C(\tau_l)$ for the main chain torsion angles $\Phi$, $\Psi$, and a side chain torsion angle $X_1$ of the Thr26 residue are shown in FIGS. 6, 7, and 8, respectively, for $\tau_l \leq 100$ ps.

TABLE VI

Comparison between GSHMC and MD in efficiency for sampling of main chain torsion angles of important catalytic residues. $A_\Omega^{MD}/A_\Omega^{GSHMC}$ is the ratio of integrated autocorrelation function values obtained from MD and GSHMC simulations.

| $A_\Omega^{MD}/A_\Omega^{GSHMC}$ | Asp20 | Thr26 |
|---|---|---|
| $\Phi$ | 3.8 | 14.0 |
| $\Psi$ | 3.4 | 4.5 |

TABLE VII

Comparison between GSHMC and MD in efficiency for sampling of side chain torsion angles of important catalytic residues. $A_\Omega^{MD}/A_\Omega^{GSHMC}$ is a ratio of integrated autocorrelation function values obtained from MD and GSHMC simulations.

| $A_\Omega^{MD}/A_\Omega^{GSHMC}$ | Glu11 | Asp20 | Thr26 |
|---|---|---|---|
| $\chi 1$ | 5.54 | 1.0 | 2.69 |
| $\chi 2$ | 7.11 | 1.56 | NA |
| $\chi 3$ | 3.76 | NA | NA |

Computed integrated autocorrelation function values, $A_\Omega$, are based on autocorrelation functions $C(\tau_l)$ and $\tau_l \leq 500$ ps. Ratios of integrated autocorrelations function values for the main chain torsion angles $\Phi$, $\Psi$ and side chain torsion angles $X_1$, $X_2$, $X_3$ for residues Asp20, Glu11 and Thr26, as observed during GSHMC and MD simulations, are presented in table VI and table VII, respectively. As shown in tables VI and VII, GSHMC requires less (up to 14 times!) iterations (MD steps) than standard MD to achieve one statistically independent sample for all torsion angles of catalytic residues Asp20, Glu11 and Thr26.

VIII. SUMMARY

We have presented a more efficient implementation of the GHMC method, which is based on the use of modified energies. The resulting GSHMC/GS2HMC methods allow the user to either perform pure sampling or stochastic dynamics simulations.

In the case of sampling, the GS2HMC method has the advantage of keeping the acceptance rate in the PMMC step high without having to make $\phi$ smaller as the system size increases.

However, the transformation step (41) requires additional force field evaluations. Repeated application of the PMMC step with a reduced value of $\phi$ and $\bar{p} = p$, i.e. no transformation, provides a viable alternative.

The GS2HMC method behaves similarly to the recently proposed S2HMC method. An advantage of GS2HMC over S2HMC is that it can be combined with higher-order (higher than fourth order) modified energies and that it can be used with partial momentum refreshment. To take full advantage of higher-order modified energies, the force field evaluations have to be performed accurately enough and sufficiently smooth cut-off functions need to be implemented.

For small values of $\phi = \sqrt{2\gamma \Delta t}$, i.e. stochastic dynamics simulations, the GSHMC method without the transformation (41) is to be recommended since the acceptance rate in the PMMC step of GSHMC is high for small values of $\phi$ and since GSHMC is cheaper to implement than GS2HMC.

Numerical experiments have demonstrated that GSHMC/GS2HMC are suitable for NVT as well as NPT simulations. In particular, we have shown that GSHMC/GS2HMC outperform both classical MD as well as standard HMC in terms of sampling. Furthermore, GSHMC provides a statistically rigorous simulation tool for stochastic dynamics in an NVT or NPT ensemble.

IX. IMPLEMENTATION AS A COMPUTER PROGRAM

In any of the above aspects, the various features may be implemented in hardware, or as software modules running on one or more processors. Features of one aspect may be applied to any of the other aspects.

The invention also provides a computer program or a computer program product for carrying out any of the methods described herein, and a computer readable medium having stored thereon a program for carrying out any of the methods described herein. A computer program embodying the invention may be stored on a computer-readable medium, or it could, for example, be in the form of a signal such as a downloadable data signal provided from an Internet website, or it could be in any other form.

Appendix 1

We derive the sixth-order modified energy. Following the approach of section IV A we first derive a modified Lagrangian density to sixth order:

$$\mathcal{L}_{\Delta t} = \frac{1}{4}\left(\sum_{i=1}^{\infty}\frac{\Delta t^{i-1}}{i!}Q^{(i)}\right) \cdot \left[\mathcal{M}(Q)\left(\sum_{i=1}^{\infty}\frac{\Delta t^{i-1}}{i!}Q^{(i)}\right)\right] + \quad (74)$$
$$\frac{1}{4}\left(\sum_{i=1}^{\infty}\frac{(-1)^{i-1}\Delta t^{i-1}}{i!}Q^{(i)}\right) \cdot \left[\mathcal{M}(Q)\left(\sum_{i=1}^{\infty}\frac{(-1)^{i-1}\Delta t^{i-1}}{i!}Q^{(i)}\right)\right] -$$
$$V(Q), = \mathcal{L} + \Delta t^2 \delta\mathcal{L}^{[4]} + \Delta t^4 \delta\mathcal{L}^{[6]} + \mathcal{O}(\Delta t^6)$$

where $\mathcal{L}$ is given by (2), $\delta\mathcal{L}^{[4]}$ by (30), and $\delta\mathcal{L}^{[6]}$ by $$\delta\mathcal{L}^{[6]} = \frac{1}{720}\left\{\begin{array}{c} 6\dot{Q}\cdot[\mathcal{M}(Q)Q^{(5)}] + 15\ddot{Q}\cdot \\ [\mathcal{M}(Q)Q^{(4)}] + 20Q^{(3)}\cdot[\mathcal{M}(Q)Q^{(3)}] \end{array}\right\}. \quad (75)$$

Hence, we define the sixth-order modified Lagrangian density by $$\mathcal{L}_{\Delta t}^{[6]} = \mathcal{L} + \Delta t^2 \delta\mathcal{L}^{[4]} + \Delta t^4 \delta\mathcal{L}^{[6]} \quad (76)$$

and higher-order modified Lagrangian can be found by including higher-order terms in the expansion (74). The sixth-order modified energy is now given by $$\mathcal{H}_{\Delta t}^{[6]} = \sum_{i=1}^{5}\left\{\sum_{j=0}^{i-1}(-1)^j\left[\frac{d^j}{dt^j}\frac{\partial \mathcal{L}_{\Delta t}^{[6]}}{\partial Q^{(i)}}\right]\cdot Q^{(i-j)}\right\} - \mathcal{L}_{\Delta t}^{[6]} \quad (77)$$

with the generalization to higher-order again being straightforward.

Appendix 2

The GSHMC method can be used to solve statistical inference problems in the same manner as the hybrid Monte Carlo (HMC) method can be applied to such problems (see, e.g., [36,37]). In particular, in a Bayesian framework, all inference problems can be reduced to the evaluation of certain expectation values with respect to the posterior distribution of unknown variables. This target posterior distribution can always be written out explicitly, up to a normalization constant, as $$\pi(q)f(y|q)\pi_0(q) \equiv \exp(-V(q)) \quad (1)$$

where f is the probabilistic model that connects data y with unknown parameters q, $\pi_0$ is the prior distribution in q (which is often assumed to be Gaussian), and $$V(q) = -\log f(y|q) - \log \pi_0(q). \quad (2)$$

In order to use the GSHMC to sample the posterior distribution (1), we introduce an auxiliary 'momentum' variable p, a (constant) symmetric mass matrix M and the 'guide Hamiltonian'

$$\mathcal{H} = \frac{1}{2}p[M^{-1}p] + V(q) \quad (3)$$

with associated Newtonian equations of motion $$\dot{q} = M^{-1}p, \quad \dot{p} = -\nabla_q V(q). \quad (4)$$

These equations can be integrated in time by a symplectic and time-reversible method such as Störmer-Verlet. The resulting propagator $U_\tau$ with appropriate reference Hamiltonian $\mathcal{H}_{\Delta t}$, is then to be used in the MDMC part of the GSHMC method. The PMMC part and the re-weighting procedure for expectation values remain unchanged.

[1] S. Duane, A. Kennedy, B. Pendleton, and D. Roweth, Phys. Lett. B 195, 216 (1987).
[2] B. Mehlig, D. Heermann, and B. Forrest, Phys. Rev. B 45, 679 (1992).
[3] J. Izaguirre and S. Hampton, J. Comput. Phys. 200, 581 (2004).
[4] G. Benettin and A. Giorgilli, J. Stat. Phys. 74, 1117 (1994).
[5] E. Hairer and C. Lubich, Numer. Math. 76, 441 (1997).
[6] S. Reich, SIAM J. Numer. Anal. 36, 475 (1999).
[7] B. Leimkuhler and S. Reich, Simulating Hamiltonian Dynamics (Cambridge University Press, Cambridge, 2005).
[8] E. Hairer, C. Lubich, and G. Wanner, Geometric Numerical Integration (Springer-Verlag, Berlin Heidelberg, 2002).
[9] B. Moore and S. Reich, Numer. Math. 95, 625 (2003).
[10] R. Skeel and D. Hardy, SIAM J. Sci. Comput. 23, 1172 (2001).
[11] C. Sweet, S. Hampton, and J. Izaguirre, Tech. Rep. TR-2006-09, University of Notre Dame (2006).
[12] C. Sweet, S. Hampton, R. Skeel, and J. Izaguirre, Tech. Rep., University of Notre Dame (2007).
[13] E. Akhmatskaya and S. Reich, in New Algorithms for Macromolecular Simulations, edited by B. L. et at (Springer-Verlag, Berlin, 2006), vol. 49 of Lecture Notes in Computational Science and Engineering, pp. 145-158.
[14] A. Horowitz, Phys. Lett. B 268, 247 (1991).
[15] A. Kennedy and B. Pendleton, Nucl. Phys. B 607, 456 (2001).
[16] H. Andersen, J. Chem. Phys. 72, 2384 (1980).
[17] S. Feller, Y. Zhang, R. Pastor, and B. Brooks, J. Chem. Phys. 103, 4613 (1995).
[18] M. Allen and D. Tildesley, Computer Simulation of Liquids (Clarendon Press, Oxford, 1987).
[19] R. MacKay, in The dynamics of numerics and the numerics of dynamics, edited by D. Broom-head and A. Iserles (Clarendon Press, Oxford, 1992), pp. 137-193.
[20] S. Gupta, A. Irbäck, F. Karsch, and B. Pterersson, Phys. Lett. B 242, 437 (1990).

[21] R. Burden and J. Faires, Numerical Analysis (Brooks Cole, 2004), 8th ed.
[22] J. Ryckaert, G. Ciccotti, and H. Berendsen, J. Comput. Phys. 23, 327 (1977).
[23] R. Faller and J. de Pablo, J. Chem. Phys. 116, 55 (2002).
[24] A. Brunger, C. Brooks, and M. Karplus, Chem. Phys. Lett. 105 (1984).
[25] H. Berendsen, J. Postma, W. van Gunsteren, A. DiNola, and J. Haak, J. Chem. Phys. 81, 3684 (1984).
[26] H. Berendsen, J. Postma, W. van Gunsteren, and J. Hermans, in Intermolecular Forces, edited by B. Pullman (D. Reidel Publishing Company, Dordrecht, 1981), pp. 331-342.
[27] E. Lindahl, B. Hess, and D. Spoel, J. Mol. Modeling 7, 305 (2001).
[28] T. Darden, D. York, and L. Pedersen, J. Chem. Phys. 98, 10089 (1993).
[29] U. Essmann, L. Perera, M. L. Berkowitz, T. Darden, H. Lee, and L. G. Pedersen, J. Chem. Phys. 103, 8577 (1995).
[30] W. Humphrey, A. Dalke, and K. Schulten, J. Molec. Graphics p. 33 (1996).
[31] W. Anderson, M. Grutter, S. Remington, L. Weaver, and B. Matthews, J. Mol. Biol 147, 523 (1981).
[32] L. Hardy and A. Poteete, Biochemistry 30, 9457 (1991).
[33] R. Kuroki, L. Weaver, and B. Matthews, Science 262, 2030 (1993).
[34] R. Kuroki, L. Weaver, and B. Matthews, Nat. Struct. Biol. 2, 1007 (1995).
[35] R. Kuroki, L. Weaver, and B. Matthews, Proc. Natl. Acad. Sci. 96, 8949 (1999).
[36] R. Neal, *Bayesian learning for neural networks* (Springer-Verlag, New York, 1996).
[37] J. Liu, *Monte Carlo Strategies, in Scientific Computing* (Springer-Verlag, New York, 2001).

The invention claimed is:

1. A method of simulating behaviour of a molecular system with m degrees of freedom over time comprising:
   a partial momentum refreshment operation performed by a computer and a molecular dynamics operation performed by a computer,
   wherein the partial momentum refreshment operation comprises:
      given a starting position q and a starting momentum p of the molecular system, partially refreshing the momentum to define refreshed momentum p' using a noise vector u, where:

$$\begin{pmatrix} u' \\ p' \end{pmatrix} = \begin{pmatrix} \cos(\phi) & \sin(\phi) \\ \sin(\phi) & -\cos(\phi) \end{pmatrix} \begin{pmatrix} u \\ p \end{pmatrix}$$

where
p', p: refreshed and current momentum,
$0 \leq \phi \leq \pi/2$,
u', u: new and current noise vectors,
$u = \beta^{-1/2} \mathcal{M}(q)^{1/2} \xi$, $\xi_i \sim N(0,1)$, $i=1,\ldots,m$, $N(0,1)$ denoting the normal distribution with zero mean and unit variance,
$\mathcal{M}$: mass matrix,
$\beta = 1/K_B T$ where T is temperature;
evaluating the shadow Hamiltonian $\mathcal{H}_{\Delta t}$ at position q and momentum p'; and
accepting or rejecting the refreshed momentum p' according to a Metropolis-type function and if p' is accepted using p' as the resulting momentum p and starting position q as the resulting position q or if it is rejected, using p as the resulting momentum p and starting position q as the resulting position;
and
wherein the molecular dynamics operation comprises:
   given a starting position q and starting momentum p of the molecular system, running a molecular dynamics simulation over a fixed number of iterations and obtaining new position q' and refreshed momentum p';
   evaluating the shadow Hamiltonian $\mathcal{H}_{\Delta t}$ at position q' and momentum p' after the molecular dynamics simulation; and
   accepting or rejecting the new system configuration produced by the molecular dynamics simulation according to a Metropolis-type function and, if the new system configuration is accepted, using q' as the resulting position q and p' as the resulting momentum p or, if it is rejected, using the original starting position q as the resulting position q and negating the original starting momentum p to give the resulting momentum p;
wherein either the partial momentum refreshment or the molecular dynamics operation is a first operation of the method, and the resulting position and resulting momentum of the first operation provides the starting position q and starting momentum p for a next operation.

2. A method according to claim 1, wherein the entire method is repeated at least once, in a same order.

3. A method according to claim 1, wherein the first operation in the method is the partial momentum refreshment operation.

4. A method according to claim 1, wherein the partial momentum refreshment operation constitutes a multiple partial momentum refreshment operation, in which the entire partial moment refreshment operation is repeated a selected number of times consecutively, to provide a final resulting momentum.

5. A method according to claim 1, wherein $\phi = \pi/2$ and the method is suitable for sampling without preserving dynamic information.

6. A method according to claim 1, wherein $\phi = \sqrt{2\gamma\tau} \ll 1$, where
$\gamma$: collision frequency constant;
$\tau = L\Delta t$, where
L: chosen number of molecular dynamics iterations;
$\Delta t$: time step;
and the method recovers statistically rigorous stochastic Langevin dynamics.

7. A method according to claim 6, wherein L is chosen to be equal to 1 to implement the Langevin Monte Carlo algorithm.

8. A method according to claim 1, wherein a value of parameter $\phi$ in the momentum refreshment operation is decided separately for each molecule in the system.

9. A method according to claim 1, wherein $\bar{p}$, a modified value for momentum p, is used in the partial momentum refreshment operation to give:

$$\begin{pmatrix} u' \\ \bar{p}' \end{pmatrix} = \begin{pmatrix} \cos(\phi) & -\sin(\phi) \\ \sin(\phi) & \cos(\phi) \end{pmatrix} \begin{pmatrix} u \\ \bar{p} \end{pmatrix}.$$

10. A method according to claim 9, wherein the modified value for momentum P is a function of momentum and position over time, preferably given by $\bar{p}=\psi(q,p,\Delta t)$; and more preferably given by $$\bar{p} = \psi(q, p, \Delta t) := p - \frac{\Delta t}{24}(\nabla_q V(q^+) - \nabla_q V(q^-))$$

where $\psi$ is a map which is invertible in the momentum vector p and $\Delta_q V$ is the derivative of the potential energy V with respect to q.

11. A method according to claim 1, wherein the refreshed momentum p' is accepted with probability $$P(q, p, u, p', u') = \min\left(1, \frac{\exp\left(-\beta\left[\mathcal{H}_{\Delta t}(q, p') + \frac{1}{2}(u')^T \mathcal{M}(q)^{-1} u'\right]\right)}{\exp\left(-\beta\left[\mathcal{H}_{\Delta t}(q, p) + \frac{1}{2}u^T \mathcal{M}(q)^{-1} u\right]\right)}\right)$$

where
p',p: refreshed and current momentum;
u',u: new and current vectors of auxiliary variables $u=\beta^{-1/2}\mathcal{M}(q)^{1/2}\xi$;
$u=\beta^{-1/2}\mathcal{M}(q)^{1/2}\xi$, $\xi_i \sim N(0,1)$, $i=1, \ldots, m$; $\mathcal{M}$: mass matrix; $\beta=1/K_B T$; and $\mathcal{H}_{\Delta t}$ is a shadow Hamiltonian.

12. A method according to claim 1, wherein each molecular dynamics iteration includes describing the forces on the atoms of the molecules of the molecular system using a chosen force field, integrating Newton's equation to predict the positions and velocities at a new time and recalculation of the forces.

13. A method according to claim 1, wherein Newton's equation of motion in the molecular dynamics operation is solved using a time reversible and symplectic method, preferably the generalized Störmer-Verlet method, more preferably the standard Störmer-Verlet method.

14. A method according to claim 1, wherein the new position q' and refreshed momentum p' in molecular dynamics simulation are accepted with probability $P(q,p,q',p')=\min(1, \exp(-\beta\{\mathcal{H}_{\Delta t}^{[4]}(q,p')-\mathcal{H}_{\Delta t}^{[4]}(q,p)\}))$.

15. A method according to claim 1, wherein calculated properties are re-weighted at the end of the entire method.

16. A method according to claim 15, wherein the re-weighting is performed using $$\langle \Omega \rangle = \frac{\sum_{i=0}^{K} w_i \Omega_i}{\sum_{i=0}^{K} w_i}$$

$w_i = \exp(-\beta\{\mathcal{H}_{(q_i,p_i)} - \mathcal{H}_{\Delta t}(q_i,p_i)\})$ where values $\mathcal{H}$ is a true Hamiltonian and $\mathcal{H}_{\Delta t}$ is a shadow Hamiltonian $\Omega$, $i=0, \ldots, K$, along a sequence of states $(q_i, p_i)$, $i=1, \ldots, K$ of any property of the system computed by the method.

17. A method according to claim 1, wherein shadow Hamiltonians $\mathcal{H}$ of an appropriate order $p=2k \geq 4$, $k=1, 2, \ldots$ of approximation are used.

18. A method according to claim 1, wherein the simulation conditions provided correspond to an NVT (canonical) ensemble.

19. A method according to claim 18, wherein the simulation in the molecular dynamics operation corresponds to an NVE (microcanonical) ensemble.

20. A method according to claim 1, wherein the simulation conditions provided correspond to an NPT (isobaric-isothermal) ensemble.

21. A method according to claim 20, wherein the simulation in the molecular dynamics operation corresponds to an NPE (isobaric) ensemble.

22. A method according to claim 1, further comprising an operation of initially inputting simulation conditions and/or simulation parameters.

23. A method according to claim 22, wherein the simulation conditions include at least one of volume, mass, temperature, pressure, number of molecules and total energy.

24. A method according to claim 22, wherein the simulation parameters include at least one of the number of repetitions of partial momentum operation and molecular dynamics operation, the order of shadow Hamiltonians used, the time step in molecular dynamics, the number of molecular dynamics iterations, the starting position and momentum for the first operation in the method, the force field parameters and the constant for partial momentum refreshment.

25. A method according to claim 1, wherein the partial momentum refreshment operation is applied to the "piston" momentum only, where "piston" is associated with the fluctuating volume of the molecular system at constant pressure.

26. A method according to claim 1, wherein the method is carried out using generalised co-ordinates.

27. A method according to claim 1, carried out by the computer.

28. A method according to claim 1, including the operation of displaying the results on a screen or printout.

29. A method of molecular simulation of a system over time comprising:
modelling the system using an atomistic model;
carrying out the method, by a computer, of simulating behaviour of a molecular system according to any of the preceding claims; and
analysing the results obtained from the simulation and relating them to macroscopic level properties.

30. A method according to claim 29, further comprising using the relationship of the results to the macroscopic properties to assess and optionally modify the system at the macroscopic level, before repeating the method on the modified system.

31. An apparatus which simulates behaviour of a molecular system with m degrees of freedom over time, comprising:
a display displaying simulation results; and
a computer performing partial momentum refreshment carrying out a partial momentum refreshment operation and molecular dynamics carrying out a molecular dynamics operation,
wherein the partial momentum refreshment comprises:
given a starting position q and a starting momentum p of the molecular system, partially refreshing the momentum to define refreshed momentum p' using a noise vector u, where:

$$\begin{pmatrix} u' \\ p' \end{pmatrix} = \begin{pmatrix} \cos(\phi) & \sin(\phi) \\ \sin(\phi) & -\cos(\phi) \end{pmatrix} \begin{pmatrix} u \\ p \end{pmatrix}$$

where
p', p: refreshed and current momentum,
$0 \leq \phi \leq \pi/2$, u', u: new and current noise vectors,
$u=\beta^{-1/2}\mathcal{M}(q)^{1/2}\xi$, $\xi_i \sim N(0,1)$, $i=1,\ldots,m$, $N(0,1)$ denoting the normal distribution with zero mean end unit variance,
$\mathcal{M}$: mass matrix,
$\beta=1/K_B T$ where T is temperature;
evaluating the shadow Hamiltonian $\mathcal{H}_{\Delta t}$ at position q and momentum p'; and
accepting or rejecting the refreshed momentum p' according to a Metropolis-type function and if p' is accepted using p' as the resulting momentum P and starting position q as the resulting position q or if it is rejected, using p as the resulting momentum p and starting position q as the resulting position;
and
wherein the molecular dynamics comprises:
given a starting position q and starting momentum p of the molecular system, running a molecular dynamics simulation over a fixed number of iterations and obtaining new position q'and refreshed momentum p';
evaluating the shadow Hamiltonian $\mathcal{H}_{\Delta t}$ at position q' and momentum p' after the molecular dynamics simulation; and
accepting or rejecting the new system configuration produced by the molecular dynamics simulation according to a Metropolis-type function and, if the new system configuration is accepted, using q' as the resulting position q and p' as the resulting momentum p or, if it is rejected, using the original starting position q as the resulting position q and negating the original starting momentum p to give the resulting momentum p;
wherein the apparatus is configured such that either the partial momentum refreshment or the molecular dynamics is a first operation of the method, and the resulting position and resulting momentum of the first operation provides the starting position q and starting momentum p for a next operation.

32. A method of solving a statistical inference problem by sampling positions q according to a given probability distribution function of the general form $p(q) \propto \exp(-\beta V(q))$, where V is a user defined cost function and $\beta$ is a parameter, using canonical momentum p, mass matrix M, and Hamiltonian energy $\mathcal{H}=\frac{1}{2}p^T \mathcal{M}^{-1} p + V(q)$, where the mass matrix depends on the positions q and the associated dynamics in (q,p) is of conservative, Newtonian form; the method comprising:
generating, by a computer, a sequence of states $(q_i, p_i)$ with respect to the canonical distribution function for a shadow Hamiltonian in two separate Markov chain Monte Carlo operations, a partial momentum refreshment Monte Carlo operation and a conservative dynamics refreshment Monte Carlo operation,
wherein the partial momentum refreshment Monte Carlo operation comprises:
given a starting position q and a starting momentum p of the system, partially refreshing the momentum to define refreshed momentum p' using a noise vector where:

$$\begin{pmatrix} u' \\ p' \end{pmatrix} = \begin{pmatrix} \cos(\phi) & -\sin(\phi) \\ \sin(\phi) & \cos(\phi) \end{pmatrix} \begin{pmatrix} u \\ p \end{pmatrix}$$

p', p: refreshed and current momentum;
$0 \leq \phi \leq \pi/2$,
u', u: new and current noise vectors,
$u=\beta^{-1/2}\mathcal{M}(q)^{1/2}\xi$, $\xi_i \sim N(0,1)$, $i=1,\ldots,m$, $N(0,1)$ denoting the normal distribution with zero mean and unit variance;
m: number of degrees of freedom of the system;
evaluating the shadow Hamiltonian $\mathcal{H}_{\Delta t}$ at position q and refreshed momentum p' according to a Metropolis-type function and if p' is accepted using p' as the resulting momentum and starting position q as the resulting position or if it is rejected, using p as the resulting momentum p and starting position q as the resulting position;
and
wherein the conservative dynamics operation comprises:
given a starting position q and starting momentum p performing a conservative dynamics simulation with a time-reversible and simplectic method over a fixed number of iterations and obtaining new position q'and refreshed momentum p';
evaluating the shadow Hamiltonian $\mathcal{H}_{\Delta t}$ at q' and momentum p' after the conservative dynamics simulation; and
accepting or rejecting the new system configuration produced by the conservative dynamics simulation according to a Metropolis-type function and, if the new system configuration is accepted, using q' as the resulting position q and p' as the resulting momentum p or, if it is rejected, using the original starting position q as the resulting position q and negating the original starting momentum p to give the resulting momentum p;
wherein either the partial momentum refreshment or the conservative dynamics operation is a first operation of the method, and the resulting position and resulting momentum of the first operation provides the starting position q and starting momentum p for a next operation.

33. A method according to claim 32, further comprising approximating expectation values according to the desired probability distribution function p(q) or the Boltzmann distribution for the Hamiltonian $\mathcal{H}$, respectively, as re-weighted averages along the generated sequence of states $(q_i, p_i)$.

34. A method according to claim 32, comprising the features of claim 2.

35. A non-transitory computer readable storage for controlling a computer and comprising a computer program which, when executed on the computer, carries out the method defined in claim 1.

36. A non-transitory computer readable storage for controlling a computer and comprising a computer program which, when executed on the computer, carries out the method defined in claim 29.

37. A non-transitory computer readable storage for controlling a computer and comprising a computer program which, when executed on the computer, carries out the method defined in claim 32.

38. An apparatus which simulates behaviour of a molecular system with m degrees of freedom over time, comprising:
a display displaying simulation results; and
a computer for carrying out a partial momentum refreshment and molecular dynamics wherein the partial momentum refreshment comprises:
given a starting position q and a starting momentum p of the molecular system, partially refreshing the momentum to define refreshed momentum p' using a noise vector u, where:

$$\begin{pmatrix} u' \\ p' \end{pmatrix} = \begin{pmatrix} \cos(\phi) & \sin(\phi) \\ \sin(\phi) & -\cos(\phi) \end{pmatrix} \begin{pmatrix} u \\ p \end{pmatrix}$$

where
p', p: refreshed and current momentum,
$0 \leq \phi \leq \pi/2$,
u', u: new and current noise vectors,
$u = \beta^{-1/2} \mathcal{M}(q)^{1/2} \xi$, $\xi_i \sim N(0,1)$, $i=1, \ldots, m$, $N(0,1)$ denoting the normal distribution with zero mean end unit variance,
$\mathcal{M}$: mass matrix,
$\beta = 1/K_B T$ where T is temperature;
evaluating the shadow Hamiltonian $\mathcal{H}_{\Delta t}$ at position q and momentum p'; and
accepting or rejecting the refreshed momentum p' according to a Metropolis-type function and if p' is accepted using p' as the resulting momentum P and starting position q as the resulting position q or if it is rejected, using p as the resulting momentum p and starting position q as the resulting position;
and wherein the molecular dynamics unit comprises:
given a starting position q and starting momentum p of the molecular system, running a molecular dynamics simulation over a fixed number of iterations and obtaining new position q' and refreshed momentum p';
evaluating the shadow Hamiltonian $\mathcal{H}_{\Delta t}$ at position q' and momentum p' after the molecular dynamics simulation; and
accepting or rejecting the new system configuration produced by the molecular dynamics simulation according to a Metropolis-type function and, if the new system configuration is accepted, using q' as the resulting position q and p' as the resulting momentum p or, if it is rejected, using the original starting position q as the resulting position q and negating the original starting momentum p to give the resulting momentum p;
wherein the apparatus is configured such that either the partial momentum refreshment or the molecular dynamics is a first operation of the method, and the resulting position and resulting momentum of the first operation provides the starting position q and starting momentum p for a next operation.

39. An apparatus which simulates behaviour of a molecular system with m degrees of freedom over time, comprising:
a display displaying simulation results; and
a computer performing partial momentum refreshment carrying out a partial momentum refreshment operation and molecular dynamics carrying out a molecular dynamics operation,
wherein the partial momentum refreshment comprises:
given a starting position q and a starting momentum p of the molecular system, partially refreshing the momentum to define refreshed momentum p':
evaluating the shadow Hamiltonian $\mathcal{H}_{\Delta t}$ at position q and momentum p'; and
accepting or rejecting the refreshed momentum p' according to a Metropolis-type function and if p' is accepted using p' as the resulting momentum P and starting position q as the resulting position q or if it is rejected, using p as the resulting momentum p and starting position q as the resulting position;
and
wherein the molecular dynamics comprises:
given a starting position q and starting momentum p of the molecular system, running a molecular dynamics simulation over a fixed number of iterations and obtaining new position q' and refreshed momentum p';
evaluating the shadow Hamiltonian $\mathcal{H}_{\Delta t}$ at position q' and momentum p' after the molecular dynamics simulation; and
accepting or rejecting the new system configuration produced by the molecular dynamics simulation according to a Metropolis-type function and, if the new system configuration is accepted, using q' as the resulting position q and p' as the resulting momentum p or, if it is rejected, using the original starting position q as the resulting position q and negating the original starting momentum p to give the resulting momentum p;
wherein the apparatus is configured such that either the partial momentum refreshment or the molecular dynamics is a first operation of the method, and the resulting position and resulting momentum of the first operation provides the starting position q and starting momentum p for a next operation.

40. An apparatus which simulates behaviour of a molecular system in an NVT or NPT ensemble, with m degrees of freedom over time, comprising:
a display displaying simulation results; and
a computer performing partial momentum refreshment carrying out a partial momentum refreshment operation and molecular dynamics carrying out a molecular dynamics operation, wherein the partial momentum refreshment comprises:
given a starting position q and a starting momentum p of the molecular system, partially refreshing the momentum to define refreshed momentum p':
evaluating the shadow Hamiltonian $\mathcal{H}_{\Delta t}$ at position q and momentum p'; and
accepting or rejecting the refreshed momentum p' according to a Metropolis-type function and if p' is accepted using p' as the resulting momentum P and starting position q as the resulting position q or if it is rejected, using p as the resulting momentum p and starting position q as the resulting position;
and
wherein the molecular dynamics comprises:
given a starting position q and starting momentum p of the molecular system, running a molecular dynamics simulation over a fixed number of iterations and obtaining new position q' and refreshed momentum p';
evaluating the shadow Hamiltonian $\mathcal{H}_{\Delta t}$ at position q' and momentum p' after the molecular dynamics simulation; and
accepting or rejecting the new system configuration produced by the molecular dynamics simulation according to a Metropolis-type function and, if the new system configuration is accepted, using q' as the resulting position q and p' as the resulting momentum p or, if it is rejected, using the original starting position q as the resulting position q and negating the original starting momentum p to give the resulting momentum p;
wherein the apparatus is configured such that either the partial momentum refreshment or the molecular dynamics is a first operation of the method, and the resulting position and resulting momentum of the first operation provides the starting position q and starting momentum p for a next operation.

* * * * *

UNITED STATES PATENT AND TRADEMARK OFFICE
CERTIFICATE OF CORRECTION

| | | |
|---|---|---|
| PATENT NO. | : 7,908,129 B2 | |
| APPLICATION NO. | : 12/222382 | |
| DATED | : March 15, 2011 | |
| INVENTOR(S) | : Elena Vitalievna Akhmatskaya et al. | |

It is certified that error appears in the above-identified patent and that said Letters Patent is hereby corrected as shown below:

Title Page Item (57) Abstract Line 8 delete " $\mathcal{H}331_{\Delta t}$ " and insert -- $\mathcal{H}_{\Delta t}$ --, therefor.

Title Page Line 18 delete " $\mathcal{H}331_{\Delta t}$ " and insert -- $\mathcal{H}_{\Delta t}$ --, therefor.

Column 26, Line 66 in Claim 10, delete "P" and insert -- $\bar{P}$ --, therefor.

Column 27, Line 5 in Claim 10, delete " $\bar{p} = \psi(q, p, \Delta t) := p - \frac{\Delta t}{24}(\nabla_q V(q^+) - \nabla_q V(q^-))$ "

and insert -- $\bar{p} = \psi(q, p, \Delta t) := p - \frac{\Delta t}{24}(\nabla_q V(q^+) - \nabla_q V(q^-))$ --, therefor.

Column 27, Lines 22-23 in Claim 11 delete " $u = \beta^{-1/2} M(q)^{1/2} \xi;$ "

and insert -- $u = \beta^{-1/2} M(q)^{1/2} \xi;$ --, therefor.

Column 27, Lines 41-42 in Claim 14, delete " $P(q,p,q',p')=\min(1, \exp(-\beta\{\mathcal{H}_{\Delta t}^{[4]}(q,p') - \mathcal{H}_{\Delta t}^{[4]}(q,p)\}))$ "

and insert -- $P(q,p,q',p')=\min(1, \exp(-\beta\{\mathcal{H}_{\Delta t}^{[4]}(q,p') - \mathcal{H}_{\Delta t}^{[4]}(q,p)\}))$ --, therefor.

Column 27, Line 56 in Claim 16, delete " $w_i = \exp(-\beta\{\mathcal{H}(q_i,p_i) - \mathcal{H}_{\Delta t}(q_i,p_i)\})$ "

and insert -- $w_i = \exp(-\beta\{\mathcal{H}(q_i,p_i) - \mathcal{H}_{\Delta t}(q_i,p_i)\})$ --, therefor.

Signed and Sealed this
Seventeenth Day of May, 2011

David J. Kappos
*Director of the United States Patent and Trademark Office*

CERTIFICATE OF CORRECTION (continued)
U.S. Pat. No. 7,908,129 B2

Column 27, Line 58 in Claim 16, delete " $\mathcal{H}$is " and insert -- $\mathcal{H}$ is --, therefor.

Column 27, Line 63 in Claim 17, delete " $\mathcal{H}$is " and insert -- $\mathcal{H}$ is --, therefor.

Column 28, Line 23 in Claim 24, after "constant" insert -- $\Phi$ --.

Column 29, Line 21 in Claim 31, delete "q'and" and insert -- q' and --, therefor.

Column 30, Line 16 in Claim 32, delete "simplectic" and insert -- symplectic --, therefor.

Column 30, Line 17 in Claim 32, delete "q'and" and insert -- q' and --, therefor.

Column 31, Line 19 in Claim 38, after "dynamics" delete "unit".

Column 31, Line 23 in Claim 38 delete "q'and" and insert -- q' and --, therefor.

Column 32, Line 27 in Claim 40, after "operation," delete "wherein the partial momentum refreshment comprises:" and insert the same on Line 28, Col. 32 as a new paragraph.